United States Patent
Laster et al.

(10) Patent No.: US 11,000,021 B2
(45) Date of Patent: May 11, 2021

(54) CASTABLE SENSOR DEVICE

(71) Applicant: NAVICO HOLDING AS, Egersund (NO)

(72) Inventors: Matthew Laster, Broken Arrow, OK (US); Lucas Dale Steward, Broken Arrow, OK (US); Aaron J. Burton, Tulsa, OK (US)

(73) Assignee: NAVICO HOLDING AS, Egersund (NO)

( * ) Notice: Subject to any disclaimer, the term of this patent is extended or adjusted under 35 U.S.C. 154(b) by 315 days.

(21) Appl. No.: 16/007,058

(22) Filed: Jun. 13, 2018

(65) Prior Publication Data

US 2018/0288990 A1  Oct. 11, 2018

Related U.S. Application Data

(63) Continuation-in-part of application No. 14/628,154, filed on Feb. 20, 2015, now abandoned.

(51) Int. Cl.
| | |
|---|---|
| *A01K 85/01* | (2006.01) |
| *A01K 97/00* | (2006.01) |
| *A01K 91/20* | (2006.01) |
| *A01K 79/02* | (2006.01) |
| *G01N 33/18* | (2006.01) |

(52) U.S. Cl.
CPC .............. *A01K 85/01* (2013.01); *A01K 79/02* (2013.01); *A01K 91/20* (2013.01); *A01K 97/00* (2013.01); *G01N 33/1886* (2013.01)

(58) Field of Classification Search
CPC ........ A01K 85/01; A01K 79/02; A01K 91/20; A01K 73/045; G01N 33/1886; G01C 13/00; G06F 3/011
See application file for complete search history.

(56) References Cited

U.S. PATENT DOCUMENTS

| | | | |
|---|---|---|---|
| 5,511,335 A | 4/1996 | Langer | |
| 5,581,930 A * | 12/1996 | Langer | .................. A01K 79/02 43/17 |
| 5,816,874 A | 10/1998 | Juran et al. | |

(Continued)

FOREIGN PATENT DOCUMENTS

JP  62215889 A  9/1987

*Primary Examiner* — Regis J Betsch
*Assistant Examiner* — Kaleria Knox
(74) *Attorney, Agent, or Firm* — Nelson Mullins Riley & Scarborough LLP

(57) ABSTRACT

A sensor assembly for a castable lure is provided including a pressure sensor configured to measure a water pressure applied to the castable lure when deployed in an underwater environment, a processor, and a memory including computer program code. The computer program code configured to, when executed on the processor, cause the processor to receive pressure data from the pressure sensor, correlate the pressure data with time stamp data, cause the pressure data and correlated time stamp data to be stored in the memory, determine a data connection status between a transceiver and a marine electronic device, and in response to determining that a data connection exists, cause the pressure data and the correlated time stamp data to be transmitted to the marine electronic device. The pressure data and correlated pressure data correspond to a depth profile for a cast of the castable lure.

21 Claims, 20 Drawing Sheets

(56) References Cited

U.S. PATENT DOCUMENTS

| | | | |
|---|---|---|---|
| 6,404,204 B1 | 6/2002 | Farruggia et al. | |
| 7,380,453 B1 * | 6/2008 | Van Every | G01C 13/00 367/7 |
| 9,137,977 B2 * | 9/2015 | Davidson | A01K 85/01 |
| 2005/0032582 A1 * | 2/2005 | Mahajan | A63B 69/3632 473/222 |
| 2005/0232638 A1 | 10/2005 | Fucile et al. | |
| 2007/0058489 A1 | 3/2007 | Bratcher | |
| 2008/0192576 A1 | 8/2008 | Vosburgh et al. | |
| 2008/0279047 A1 | 11/2008 | An et al. | |
| 2011/0214500 A1 | 9/2011 | Cabrera et al. | |
| 2012/0144723 A1 | 6/2012 | Davidson | |
| 2012/0152027 A1 | 6/2012 | Wootten | |
| 2013/0187787 A1 | 7/2013 | Damus et al. | |
| 2014/0057677 A1 | 2/2014 | Liubinas et al. | |
| 2014/0224167 A1 | 8/2014 | Gasparoni et al. | |
| 2014/0301166 A1 * | 10/2014 | Skjold-Larsen | A01K 73/045 367/129 |
| 2016/0073017 A1 * | 3/2016 | Ogasawara | G06F 3/011 463/31 |
| 2016/0245649 A1 | 8/2016 | Laster et al. | |

\* cited by examiner

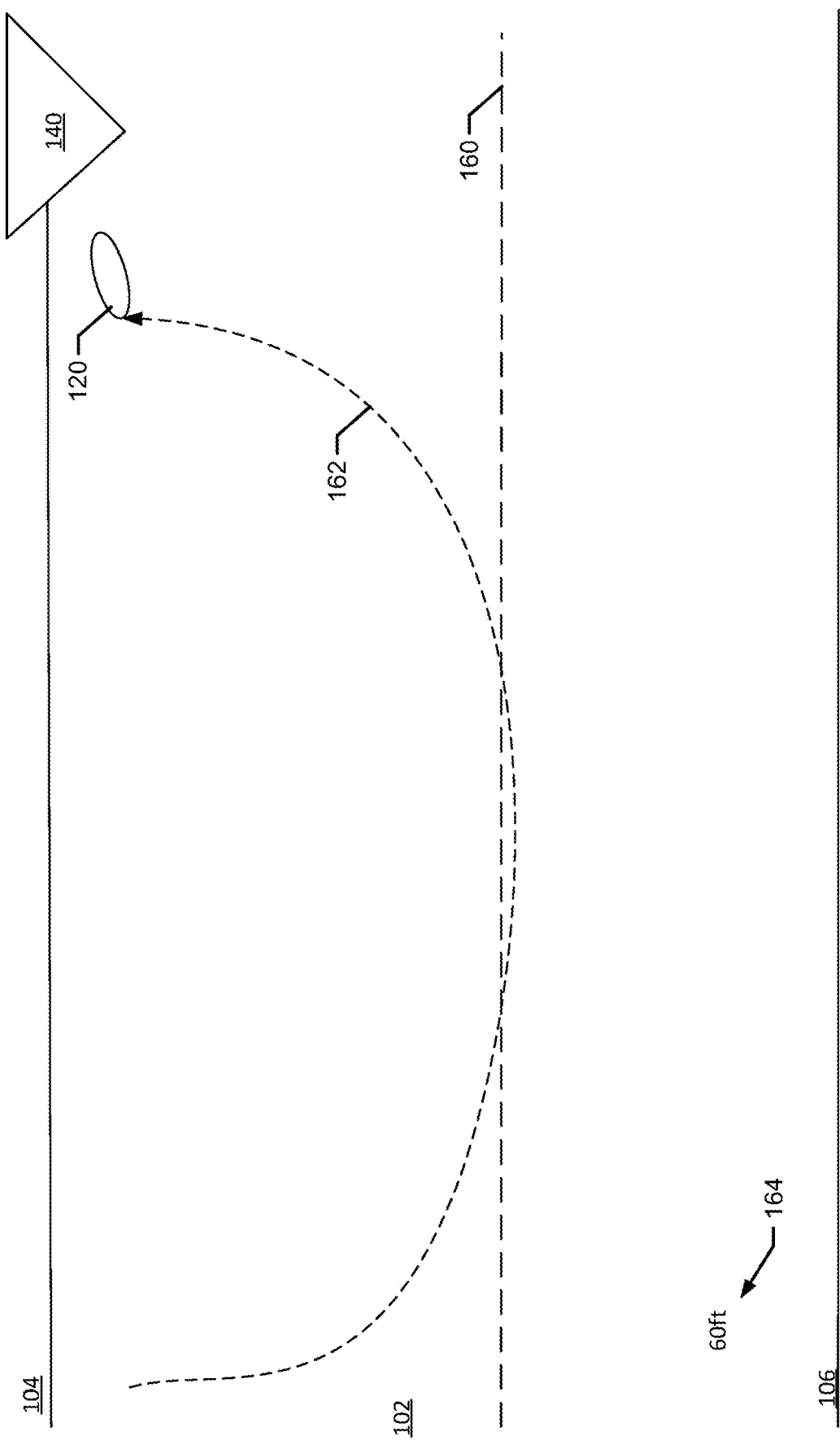

CASTABLE SENSOR DEVICE

CROSS REFERENCE TO RELATED APPLICATIONS

This application claims priority to and is a continuation-in-part of U.S. patent application Ser. No. 14/628,154, entitled "Castable Sensor Device," filed Feb. 20, 2015, which is incorporated by reference herein in its entirety.

FIELD OF THE INVENTION

Embodiments of the present invention relate generally to castable devices and, more particularly, to systems, assemblies, and associated methods for providing a castable sensor device.

BACKGROUND

Some fishing lures, such as crank bait lures, are configured to imitate a bait fish moving through the water at a target water depth. These lures are available in a wide variety of sizes and colors, most having one or more treble hooks attached on ventral side of the bait, e.g. the "belly" side (e.g., a first hook at a mid-ventral point and a second hook near or at the end of the lure). Crank bait lures also include a bill-shaped frontal protrusion, e.g. a "bill" or "lip", although some are "lipless." The size of the bill on the front of the crank bait and/or the weight of the lure determines how deep the lure will dive. Crank bait lures may also be designed to deflect side-to-side or "wobble" to further imitate a bait fish. The wobble of the lure may be determined based on the bill and/or a contour of the lure. Beyond the design of the lure, crank speed may also effect the operating depth and wobble of the lure. For example, a lure may dive deeper and wobble more than the desired target depth and wobble if the crack speed is greater than the recommended crank speed. Similarly, a lure may not dive to the target depth and/or wobble less than desired, if the crank speed is insufficient.

BRIEF SUMMARY OF THE INVENTION

When in a fishing environment, the angler may select a lure based on the lures target depth. However, once cast, the angler has no way of knowing that the lure is operating at the target depth or wobble. Similarly, when designing and testing lures, a large tank of clear water may be used to estimate the depth and wobble based on observations from outside of the tank. These external observations may include errors due to the position of the observer, e.g. parallax error, or errors due to the water interface, e.g. refraction errors, or the like.

When trolling for fish, environmental related data is useful. Communicating with a device that collects this data may be beneficial to an angler and/or lure manufacturer.

Various implementations described herein are directed to using a castable sensor device. In some implementations, various techniques described herein refer to environmental sensor technology for detecting various environmental conditions in a body of water. For instance, one or more environmental sensors may be attached to a fishing line and casted in a body of water to detect various environmental conditions at a surface outside of the water as well as in the water during ascent and descent through the water. Once deployed, the one or more environmental sensors may generate and transmit environmental data related to detected environmental conditions to an onboard computing device for display by, e.g., overlaying various environmental data on chart and sonar images. In some instances, various environmental data may include current levels of environmental conditions at particular depths, upper and lower boundary levels at particular depths, average levels through a water column, and any changes that occur throughout sensor use during a particular time period or interval. The castable sensor device may include the one or more environmental sensors and may be used in either saltwater and/or freshwater. The castable sensor device may be attached to a cast line or attached as a fishing lure. These various techniques may provide an angler desirable environmental condition data of water at various depths in a water column for adjusting location, position, and/or depth of fishing lures while fishing and before moving through a desirable area where fish may be running or holding.

In some example embodiments, the castable sensor device may be incorporated into a fishing lure, such that one or more environmental conditions may be monitored as the lure is cast and retrieved, e.g. reeled in. The environmental conditions data or sensor data may be compared to one or more fish profiles to determine if the environmental conditions and/or the travel path of the lure are conducive for catching fish generally or catching a specified type of fish. In an example embodiment, one or more actions may be determined and displayed on a user interface to increase the likelihood of successful fishing casts based on the comparison of the sensor data to the fish profiles. For example, recommending changing of crank speed, lure, bait type, or the like.

In an example embodiment, the sensor data may include pressure data and correlated time stamp data, which may be utilized to generate a depth profile of the lure for each cast. The depth profile may be displayed on the user interface to enable the user to determine if the lure is reaching or exceeding the desired or expected depth. In response to the depth profile not matching the expected depth, on ore more corrective actions may be determined and displayed for the user. Further, the environmental conditions for each cast may enable the user to more closely target a depth band in which the environmental conditions are best for the desired fish type.

In some example embodiments, the lure may include an accelerometer and gyroscope enabling angular velocity and acceleration data to be collected for each cast. The angular velocity and acceleration data may be used to generate a three dimensional cast profile for the lure. In addition to the depth of the lure the three dimensional cast profile may also include a measure of the side to side movement, or "wobble" of the lure Similar to depth profile comparison the cast profile may be compared to an expected depth and wobble and one or more corrective actions may be determined based on deviations therefrom.

In an example embodiment, the lure may include a sonar transducer configured to emit a sonar signal into the underwater environment when submerged. The sonar signal may be received by a sonar transducer associated with a water craft and plotted in the resulting sonar image. As such, the user may have a live feed of the position of the lure in the underwater environment during the cast, which may enable the user to make dynamic adjustments to the crank speed applied to the lure to change the depth or wobble of the lure. A sonar cast profile may be generated in an instance in which a plurality of plots of the sonar signal are displayed in the sonar image.

In addition to the benefits to the end user of the lure, manufacturers may also use the depth profiles, cast profiles or sonar plotting to determine deviations from the expected performance in a testing environment or user reported sensor data. The manufacture may compare the cast profile, sonar cast profile, and/or the depth profile to expected depth and wobble profiles and determine one or more modifications to the lure based on deviations from the expected depth and/or expected wobble profile.

In an example embodiment, a sensor assembly for a castable lure is provided including a pressure sensor configured to measure a water pressure applied to the castable lure when deployed in an underwater environment. The castable lure also includes a transceiver configured to transmit data from the castable lure to a marine electronic device, a processor, and a memory including computer program code. The memory and computer program code are configured to, when executed on the processor, cause the processor to receive pressure data from the pressure sensor, correlate the pressure data with time stamp data, cause the pressure data and correlated time stamp data to be stored in the memory, determine a data connection status between the transceiver and the marine electronic device, and, in response to determining that a data connection exists between the transceiver and the marine electronic device, cause the pressure data and the correlated time stamp data to be transmitted to the marine electronic device. The pressure data and correlated pressure data correspond to a depth profile for a cast of the castable lure, wherein the depth profile corresponds to a travel path of the castable lure during the cast.

In an example embodiment, the sensor assembly also includes a time of flight sensor configured to measure a time of flight of the castable lure from an initiation of the cast to the castable lure striking water. The memory and the computer program code are further configured to cause the processor to receive time of flight data from the time of flight sensor, associate the time of flight data with the pressure data and the time stamp data, and cause the time of flight data to be transmitted with the pressure data and correlated time stamp data, wherein the time of flight data corresponds to a cast distance of the depth profile.

In some example embodiments, the sensor assembly also includes a gyroscope configured to measure angular velocity of the castable lure, and an accelerometer configured to measure acceleration of the castable lure. The memory and the computer program code are further configured to cause the processor to receive angular velocity data from the gyroscope and acceleration data from the accelerometer, associate the angular velocity data and the acceleration data with the time stamp data, and cause the angular velocity data and the acceleration data to be transmitted with the pressure data and correlated time stamp data. The pressure data, the angular velocity data, the acceleration data, and the correlated time stamp data correspond to a three-dimensional cast profile for the cast of the castable lure.

In an example embodiment, the sensor assembly also includes a sonar transducer configured to emit a sonar signal into the underwater environment when the castable lure is at least partially submerged. In an example embodiment, the transceiver utilizes the sonar transducer to transmit the pressure data and the correlated time stamp data to the marine electronic device.

In some example embodiments, the transceiver includes a Bluetooth transceiver.

In some example embodiments, the sensor assembly also included at least one of a chlorophyll sensor, an oxygen sensor, a temperature sensor, a light sensor, an electrolyte sensor, and an acidity sensor.

In another example embodiment, a marine electronic device is provided including a communication interface configured to receive data from a castable lure. The castable lure comprises a pressure sensor configured to measure a water pressure applied to the castable lure when deployed in an underwater environment. The marine electronic device also includes a processor and a memory including computer program code. The memory and computer program code are configured to, when executed on the processor, cause the processor to receive pressure data and correlated time stamp data from the castable lure, determine depth data based on the pressure data, generate a depth profile for the castable lure including depth over time for a cast, and cause the depth profile to be displayed on a user interface, wherein the depth profile corresponds to a travel path of the castable lure during the cast.

In an example embodiment, the memory and the computer program code are further configured to cause the processor to receive an indication of an expected lure depth; compare the depth profile to the expected lure depth, and cause the comparison of the depth profile to the expected lure depth to be displayed on the user interface with the depth profile. In some example embodiments, the memory and the computer program code are further configured to cause the processor to determine one or more corrective actions based on the comparison of the depth profile to the expected lure depth, and cause the one or more corrective actions to be displayed on the user interface.

In some example embodiments, the castable lure also includes a time of flight sensor configured to measure a time of flight of the castable lure from an initiation of the cast to the castable lure striking water, and the memory and the computer program code are further configured to cause the processor to receive time of flight data and correlated time stamp data from the castable lure, and determine a cast distance based on the time of flight data and the associated time stamp data. The depth profile further comprises the cast distance.

In an example embodiment the castable lure also includes a gyroscope configured to measure angular velocity of the castable lure and an accelerometer configured to measure acceleration of the castable lure. The memory and the computer program code are further configured to cause the processor to receive angular velocity data and acceleration data with correlated time stamp data from the castable lure and generate a three-dimensional cast profile based on the angular velocity data and the acceleration data with associated time stamp data. In some example embodiments, the memory and the computer program code are further configured to cause the processor to receive an indication of an expected lure depth and wobble profile compare the three-dimensional cast profile to the expected lure depth and wobble profile, and cause the comparison of the three-dimensional cast profile to the expected lure depth and wobble profile to be displayed on the user interface.

In an example embodiment, the castable lure includes a sonar transducer configured to emit a sonar signal into the underwater environment when the castable lure is at least partially submerged and the memory and the computer program code are further configured to cause the processor to receive the sonar signal from the castable lure, plot the sonar signal corresponding to the castable lure in a sonar image, and cause the sonar image including the sonar signal to be displayed on a user interface. In an example embodiment, the memory and the computer program code are further configured to cause the processor to cause a plurality of plots of the sonar signal at a plurality of times to be displayed on the user interface, such that the plurality of plots renders a sonar cast profile in the sonar image. In an example embodiment, the data is received from the castable lure via sonar signal.

In some example embodiments, displaying the depth profile on the user interface comprises overlaying the depth profile on a sonar image or three-dimensional chart.

In yet a further example embodiment, a system is provided including a castable lure and a marine electronic device. The castable lure includes a pressure sensor configured to measure a water pressure applied to the castable lure when deployed in an underwater environment, a transceiver configured to transmit marine data from the castable lure to a marine electronic device, a lure processor, and a lure memory including computer program code. The lure memory and computer program code are configured to, when executed on the lure processor, cause the lure processor to receive pressure data from the pressure sensor, correlate the pressure data with time stamp data, cause the pressure data and correlated time stamp data to be stored in the lure memory, determine a data connection status between the transceiver and the marine electronic device, and, in response to determining that a data connection exists between the transceiver and the marine electronic device, causing the pressure data and the correlated time stamp data to be transmitted to the marine electronic device. The marine electronic device includes a communication interface configured to receive data from the castable lure, a device processor, and a device memory including computer program code. The device memory and computer program code are configured to, when executed on the device processor, cause the device processor to receive pressure data and correlated time stamp data from the castable lure, determine depth data based on the pressure data, and generate a depth profile for the castable lure including depth over time for a cast.

In an example embodiment, the system also includes a remote server including a server processor and a server memory including computer program code. The server memory and computer program code are configured to, when executed on the server processor, cause the server processor to receive the depth profile for the castable lure, receive an indication of an expected lure depth for the castable lure, compare the depth profile to the expected lure depth, and determine one or more recommended modifications to the castable lure based on the comparison of the depth profile to the expected lure profile.

In some example embodiments, the castable lure also includes a gyroscope configured to measure angular velocity of the castable lure and an accelerometer configured to measure acceleration of the castable lure. The device memory and the computer program code are further configured to cause the device processor to receive angular velocity data and acceleration data with associated time stamp data from the castable lure and generate a three-dimensional cast profile based on the angular velocity data and the acceleration data with the associated time stamp data. The server memory and the computer program code are further configured to cause the server processor to receive an indication of an expected lure depth and wobble profile, compare the three-dimensional cast profile to the expected lure depth and wobble profile, and determine one or more recommended modifications to the castable lure based on the comparison of the three-dimensional cast profile to the expected lure depth and wobble profile.

Additional example embodiments of the present invention include apparatuses, methods, systems, and computer program products associated with various embodiments described herein, including, for example, the above described sensor assembly and marine electronic device embodiments.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

FIGS. 2A-2C illustrate various depth profiles of a castable sensor device in accordance with various implementations described herein.

DETAILED DESCRIPTION

Various implementations of using a castable sensor device will now be described in reference to FIGS. 1A-12.

Figure 1A:
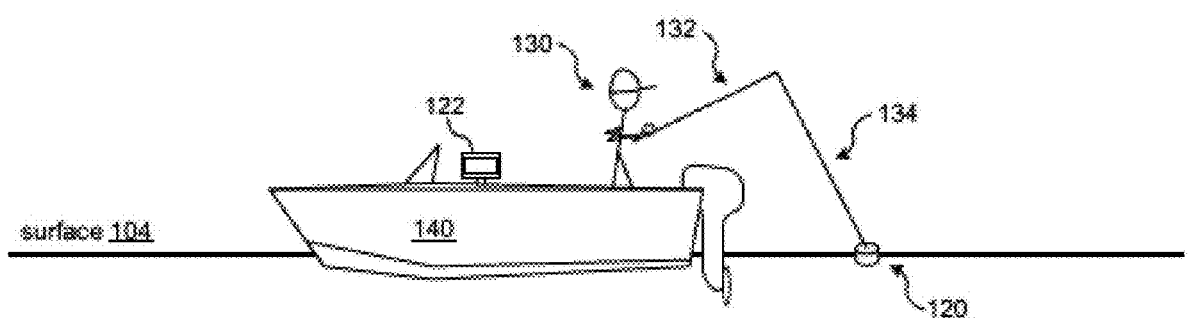
FIGS. 1A-1C illustrate various views of using a castable sensor device in accordance with various implementations described herein.
Figure 1B:
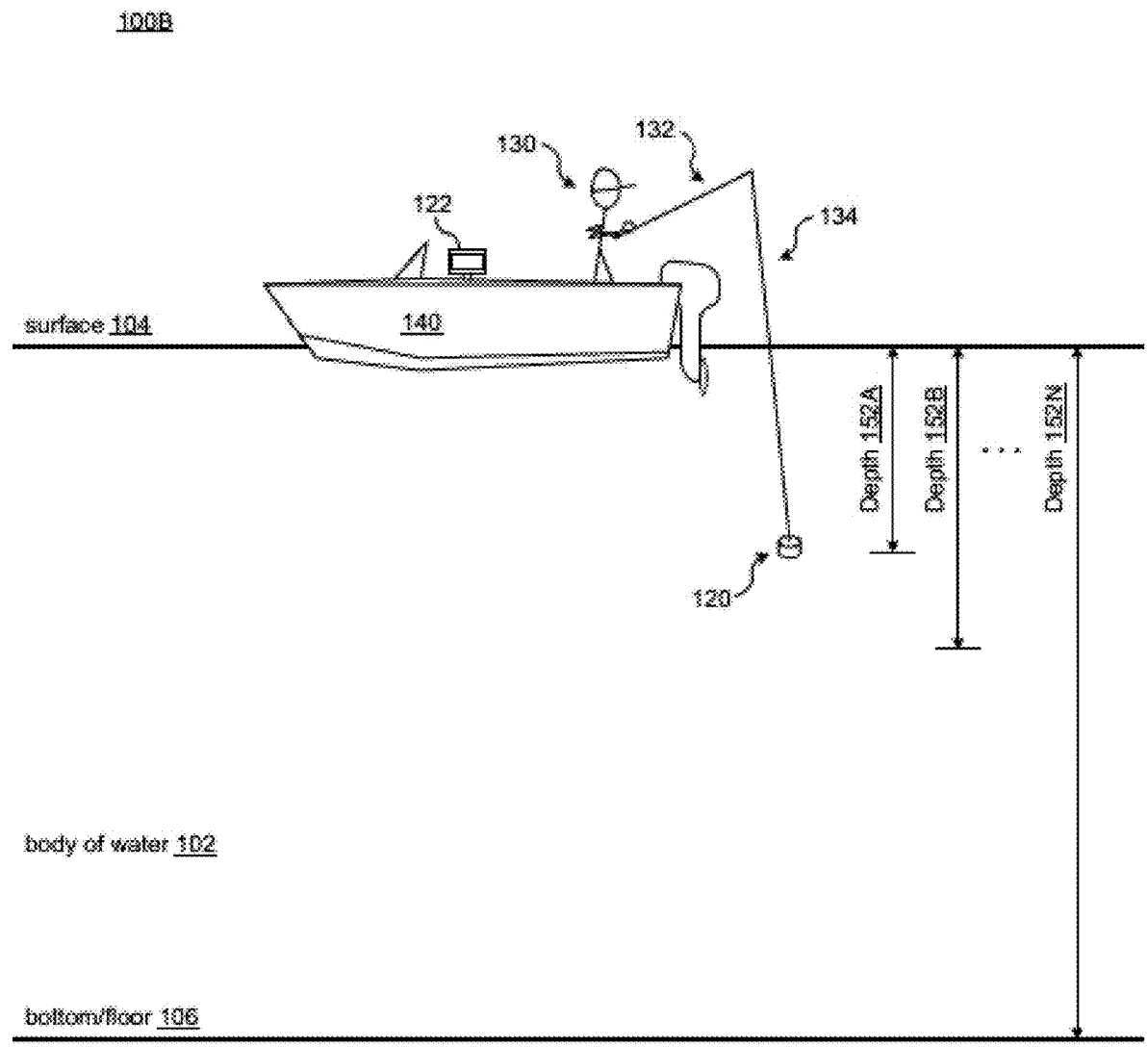
Figure 1C:
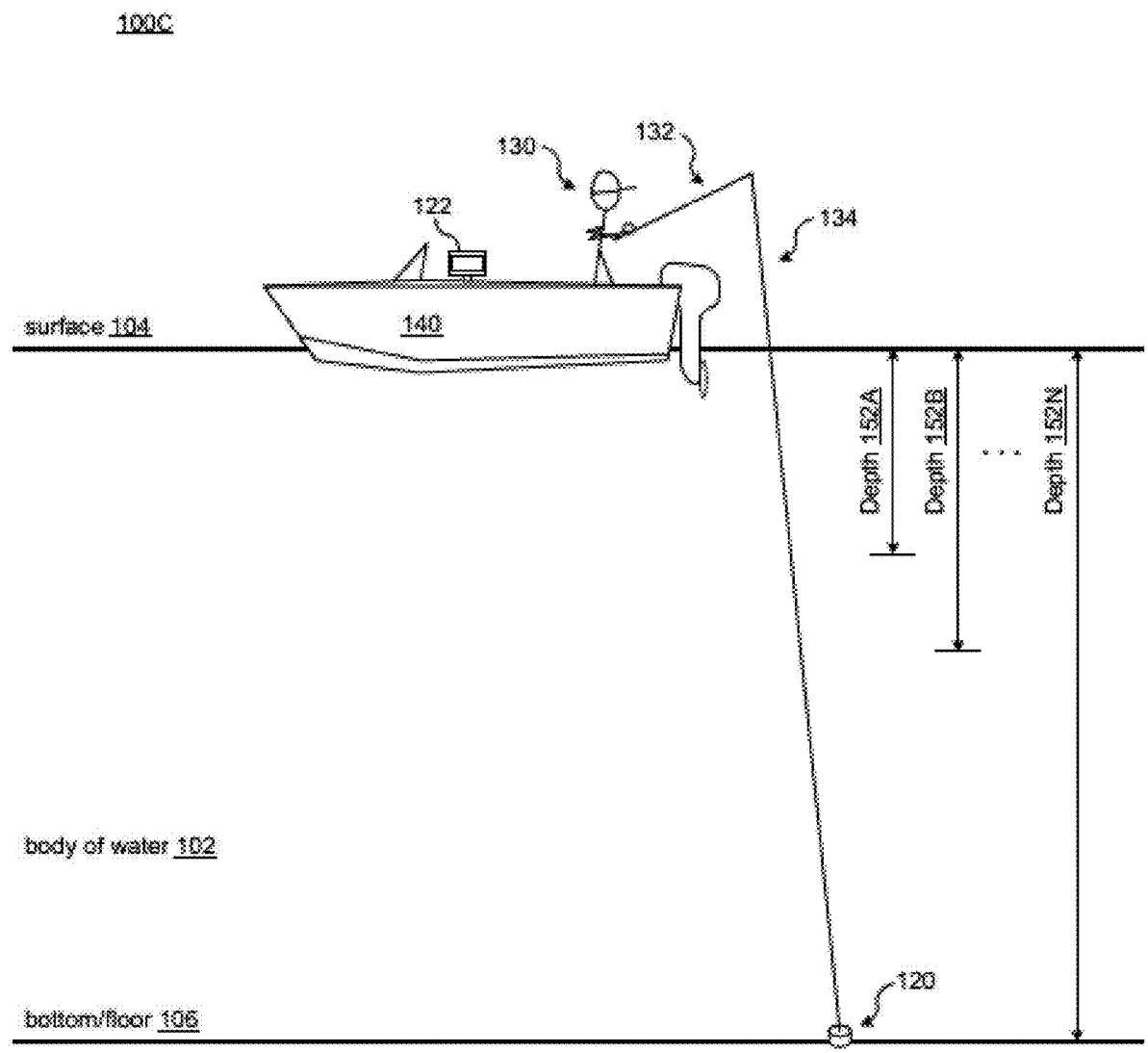

FIGS. 1A-1C illustrate various views of using a castable sensor device 120 in accordance with various implementations described herein. In particular, FIG. 1A illustrates a view of using the castable sensor device 120 at a surface 104 (e.g., zero depth) of a body of water 102, FIG. 1B illustrates another view of using the castable sensor device 120 at a depth 152A, and FIG. 1C illustrates another view of using the castable sensor device 120 at another depth 152N, such as near a bottom or floor 106 of the body of water 102.

The term "castable sensor device," "castable device," and "castable lure" generally refer to a sensor assembly which is configured to be cast into a body of water 102, such as to collect data, and may be used interchangably herein.

In reference to FIG. 1A, the castable sensor device 120 may include one or more environmental sensors configured to generate sensor data at one or more depths of the device 120 in a column of water in the body of water 102, such as, e.g., ocean, sea, gulf, lake, river, stream, pond, etc. In various implementations, the one or more environmental sensors may be configured to detect levels of environmental content, concentrations, and/or characteristics of the body of water 102 at the surface 104 and/or at various depths beneath the surface 104. For instance, the detectable environmental characteristics may include one or more of pressure (e.g., atmospheric pressure, water pressure, etc.), chlorophyll concentration, oxygen concentration, temperature, light intensity, electrolyte concentration (e.g., salt content), acidity, etc.

In some implementations, the castable sensor device 120 may include various computing, processing, and storage components, such as, e.g., at least one processor and memory. The memory may include instructions that cause the processor to receive sensor data from the one or more environmental sensors after deployment of the castable sensor device 120 in the body of water 102 and record the sensor data received from the one or more environmental sensors at one or more depths of the castable sensor device 120 in the body of water 102. In some instances, the sensor data may be received and/or recorded at one or more depths during vertical movement (e.g., ascent and/or descent) of the castable sensor device 120 in the body of water 102. In some other instances, the sensor data may be received and/or recorded at one or more depths while the castable sensor device 120 is holding or remains stationary in the body of water 102.

In some implementations, the memory may include instructions that cause the processor to transmit sensor data generated by the one or more environmental sensors and/or recorded by the processor. In some instances, the castable sensor device 120 may include a network interface, such as, e.g., a transmitter, transceiver, etc., to transmit sensor data to a computing device 122, such as, e.g., a marine electronics device, multi-function display (MFD), smart phone, computer, laptop, tablet, etc. The computing device 122 may be configured to store, record, and/or log sensor data received from the castable sensor device 120. Further, the computing device 122 may be configured to display sensor data and/or various images associated with sensor data received from the castable sensor device 120 on a display component, such as, e.g., a monitor or other computer display.

In various instances, transmission of sensor data between the castable sensor device 120 and the computing device 122 may occur via a wired or wireless communication network. Further, in some instances, transmission of sensor data between the castable sensor device 120 and the computing device 122 may occur when the castable sensor device 120 surfaces from the body of water 102. For example, the castable sensor device 120 may include a short range wireless transceiver, such as a Bluetooth transceiver, near field communication transceiver, or the like. The processor may monitor the connection status between the castable sensor device 120 and the computing device and cause the sensor data to be transmitted when the connection is established, such as when the castable sensor device 120 is removed from the body of water 102 between casts. In some other instances, transmission of sensor data between the castable sensor device 120 and the computing device 122 may occur while the castable sensor device 120 is submerged (or during submersion) underneath the surface 104 of the body of water 102 via one or more underwater wired or wireless communication channels. For example, the castable sensor device 120 may include a sonar transducer configured to transmit the sensor data to the computing device using underwater acoustic communications (UAC). The computing device 122 may receive the sensor data via a sonar transducer or dedicated UAC receiver.

The one or more environmental sensors may be configured to periodically generate sensor data at pre-determined time intervals and/or at pre-determined depth intervals. For instance, the pre-determined time intervals may refer to generating sensor data for each unit of time, such as, e.g., seconds, minutes, etc. In another instance, the pre-determined depth intervals may refer to generating sensor data for each unit of depth, such as, e.g., inches, feet, meters, etc. In some other instances, since depth may relate to pressure, the pre-determined depth intervals may refer to generating sensor data for each unit of change in water pressure, such as, e.g., Pascal's, pounds per square inch (psi), bars, atmospheres, etc.

During trolling for fish, the castable sensor device 120 including the one or more environmental sensors may be used to detect, determine, and/or identify levels of environmental content, concentrations, and/or characteristics of the body of water 102 at the surface 104 and/or at various depths beneath the surface 104. In various instances, sensor data generated by the one or more environmental sensors may be used to assist a user 130 (e.g., boat pilot, fisherman, angler, etc.) with locating or finding a desirable place to fish in the body of water 102. Generally, environmental conditions in the body of water 102 may affect where fish and/or schools of fish are holding.

Therefore, in some instances, knowing the environmental conditions in the body of water 102 beneath a vessel 140 at various depths may be beneficial to the user 130. For instance, during trolling, the castable sensor device 120 may be coupled to a casting device, such as a rod 132 (e.g., a fishing rod or pole), via a line 134 (e.g., a fishing line). The rod 132 may be configured for casting the castable sensor device 120 by the user 130. As shown in FIG. 1A, the user 130 may cast the castable sensor device 120 into the body of water 102 proximate to a stern of the vessel 140, while the user 130 is positioned within the vessel 140. However, in various other instances, the user 130 may cast the castable sensor device 120 from anywhere on the vessel 140, while the user 130 is positioned within the vessel 140. Additionally or alternatively, the castable sensor device 120 may be cast at a fishing location to determine environmental conditions of the body of water in the travel path of the castable sensor device.

In various implementations, deployment of the castable sensor device 120 in the body of water 102 may include casting the castable sensor device 120 in the body of water 102 by the user 130, as shown in FIG. 1A. Therefore, in various instances, the castable sensor device 120 may include a castable housing, such as a waterproof housing that is impervious to water. In some instances, the castable sensor device 120 may include a castable lure or fishing bait, such as a crank bait. Further, in some instances, the one or more environmental sensors of the castable sensor device 120 may be encapsulated within the waterproof housing that is impervious to water so as to protect the one or more environmental sensors from water damage. In some other implementations, each of the one or more environmental sensors may be encased in a waterproof material that is impervious to water for protection from water damage.

In one implementation, the castable sensor device 120 may be configured as a castable lure having one or more environmental sensors. For instance, the castable lure may include a first sensor, e.g. a pressure sensor, configured to determine water pressure at one or more depths of the castable lure in water (e.g., body of water 102). In this instance, the first sensor may be configured to further generate depth data based on the determined water pressure at one or more depths of the castable lure in the body of water 102. Further, the castable lure may include at least one other sensor (e.g., a second sensor) configured to generate various types of environmental data (e.g., one or more of chlorophyll concentration, oxygen concentration, temperature, light intensity, electrolyte concentration, salt content, acidity, etc.) corresponding to the depth data at the one or more depths of the castable lure in the body of water 102. Further, in some instances, the castable lure may include some type of computing component configured to record the first sensor data generated by the first sensor and the second sensor data generated by the second sensor.

Figure 3A:
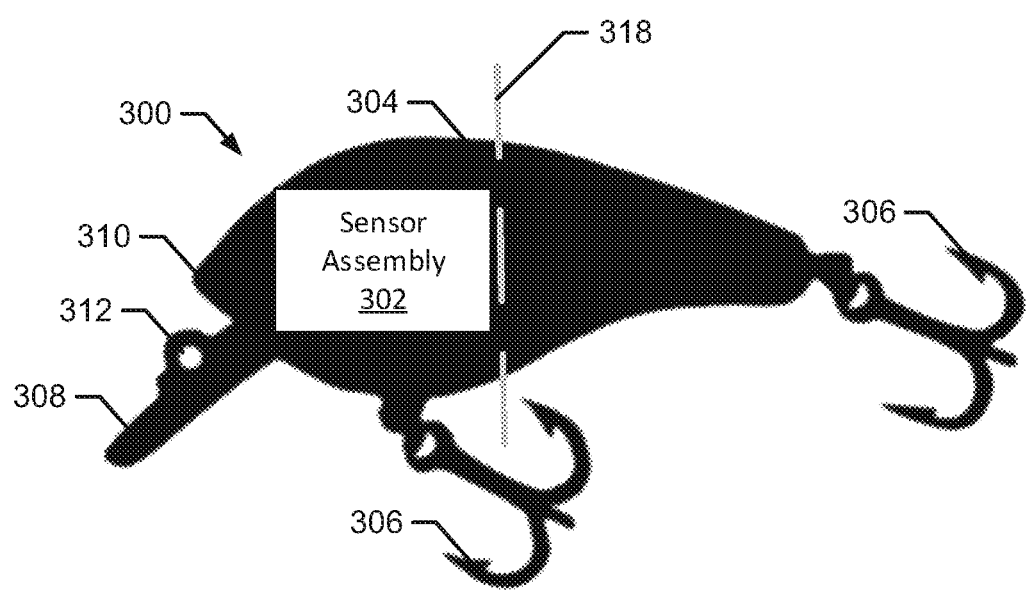
FIG. 3A illustrates a castable sensor device embodied as a crank bait lure in accordance with various implementations described herein.
Figure 3B:
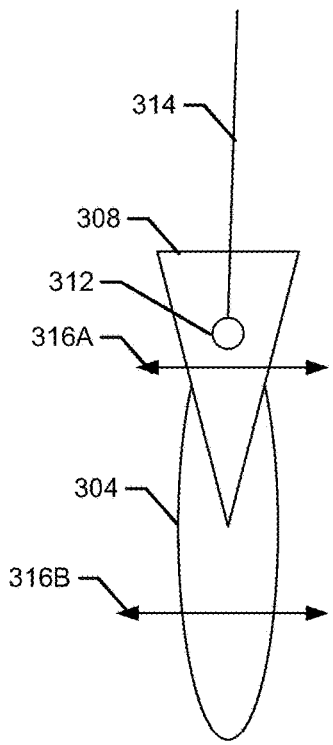
FIG. 3B illustrates another example castable sensor device in accordance with various implementations described herein.

In various implementations, the castable lure may be in the form of one or more environmental sensors being added or integrated to/with a fishing bait, whereby the environmental sensors are configured to record various depths that the fishing bait reaches on a cast or troll and/or also to collect various environmental conditions (e.g., sensed levels) at those various depths (example lures can be seen in FIGS. 3A and 3B). In an example embodiment, the sensor data may be correlated to time stamp data as it is measured, such that the sensor data may be plotted over a time period, such as during a cast. The castable lure may be configured to output environmental sensor data and information to a computing device for display. This output may be transmitted via wired or wireless communication. The displayed data and information may be for a single cast, multiple casts, and/or data combined from multiple different casts to create a depth and temperature map of an area on a body of water. Various types of fishing bait, such as, e.g., a crank bait, may be used with this castable lure technique. Further, in some instances, this castable lure technique may assist anglers and fishermen to know various lure depths on multiple cast trolls so as to assist with making changes to the manner in which reeling or holding a rod angle may be used to dial in on a particular depth that bait are running or holding. This information may assist with looking at fish depth on fish finder sonar and wanting bait fish to pass by at a same level. In some example embodiments, the depth of each cast may be plotted over time based on the correlated time stamp data as a depth profile for the castable lure.

In reference to FIGS. 1B-1C, the castable sensor device 120 may include one or more environmental sensors configured to generate sensor data at one or more depths 152A, 152B, . . . , 152N of the device 120 in a column of water beneath the surface 104 of the body of water 102. During trolling, the castable sensor device 120 including the one or more environmental sensors may be used to detect, determine, and/or identify levels of environmental content, concentrations, and/or characteristics of the water in the body of water 102 at the surface 104 and/or at the various depths 152A, 152B, . . . , 152N beneath the surface 104 and/or beneath the vessel 140.

For instance, as shown in FIG. 1B, the one or more environmental sensors of the castable sensor device 120 may be configured to generate sensor data at the depth 152A of the device 120 in a column of water beneath the surface 104 of the body of water 102. Further, as shown in FIG. 1C, the one or more environmental sensors of the castable sensor device 120 may be configured to generate sensor data at the depth 152N (e.g., near the bottom or floor 106 of the body of water 102) of the device 120 in a column of water beneath the surface 104 of the body of water 102.

In some instances, the surface 104 of the body of water 102 may be referred to as zero depth or an upper boundary of depth, and the bottom or floor 106 of the body of water 102 may be referred to as a lower boundary of depth. In some instances, the various depths 152A, 152B, . . . , 152N may refer to various depth positions, including the upper and lower boundaries, in a water column between the surface 104 and the floor 106 of the body of water 102. Therefore, in various instances, each of the one or more various depths 152A, 152B, . . . , 152N may refer to any depth position in the water column between the surface 104 and the floor 106 of the body of water 102.

Figure 2B:
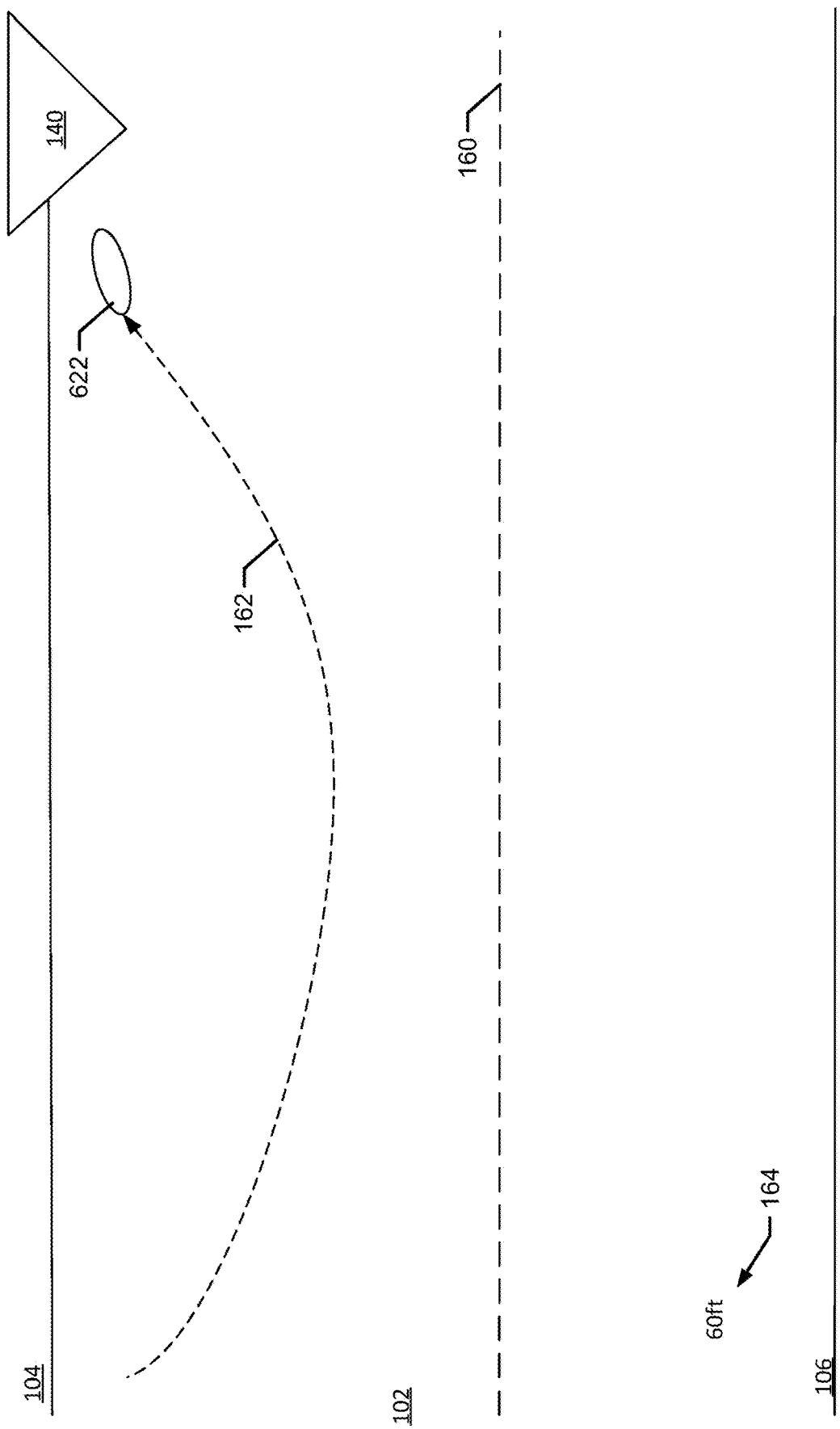
Figure 2C:
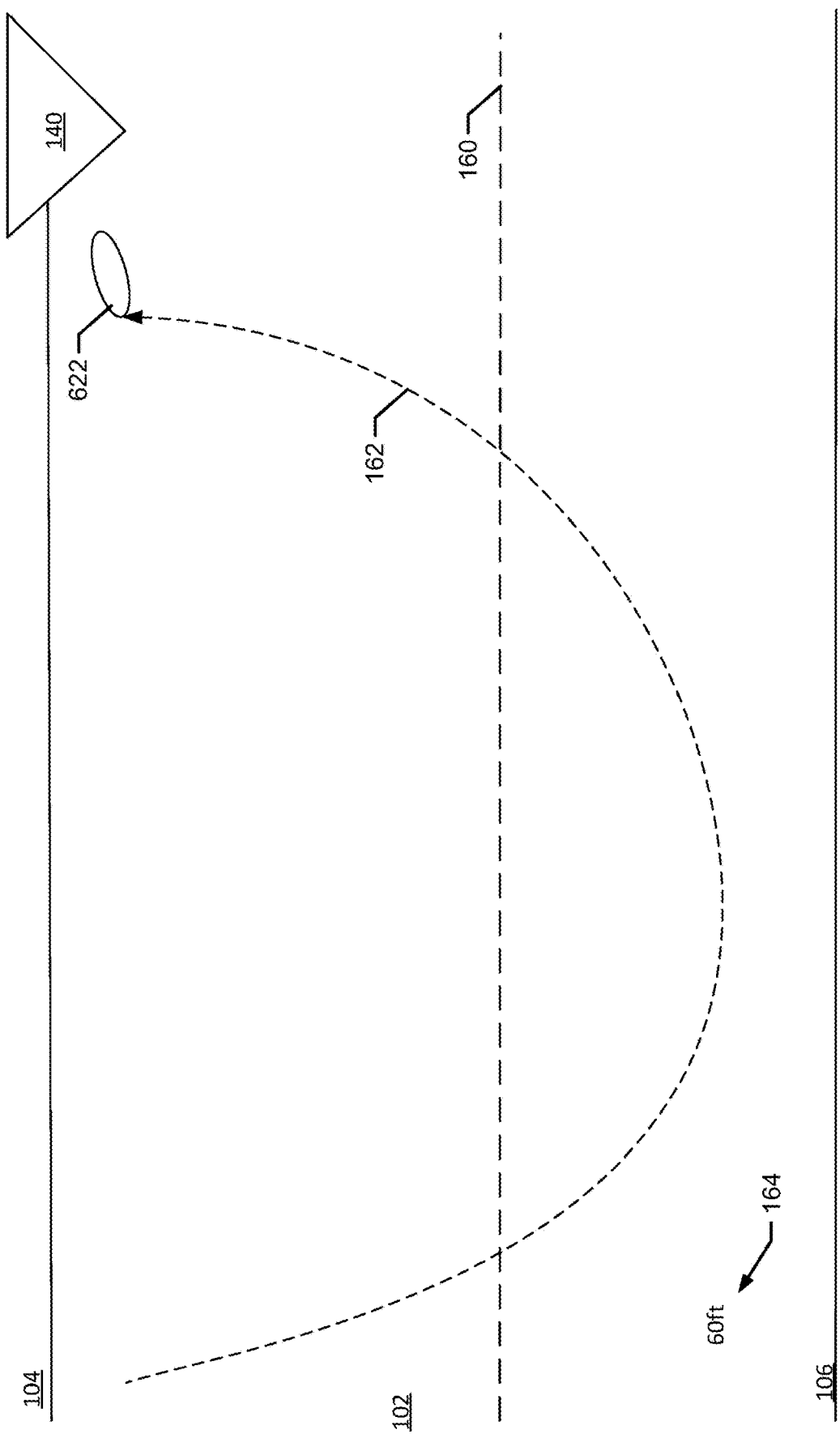

FIGS. 2A-2C illustrate example depth profiles for a castable sensor device 120, e.g. castable lure. The castable sensor device 120 may have an expected depth 160, such as the manufacturer's depth rating. The manufacturer's depth rating may be based on the width or length of a bill, or lip, of the castable sensor device 120. The depth of the castable sensor device 120 may be plotted over the time period of the cast based on the time stamp data correlated to each depth measurement, to generate a depth profile 162 for each cast. The depth profile of FIG. 2A depicts the castable sensor device 120 moving rapidly downward toward the expected depth 160, maintaining a depth near the expected depth 160 for a period and then rising near the vessel 140, as the castable lure is reeled in. In FIG. 2B, the castable lure initially moves downward but stops descending at a depth significantly less than the expected depth 160, before rising toward the vessel 140. In FIG. 2C, the castable sensor device 120 initially moves rapidly downward exceeding the expected depth 160 and maintains a depth in excess of the expected depth 160 until the castable lure 120 rises toward the vessel 140.

Turning briefly to FIGS. 3A and 3B, as discussed above, the castable sensor device 120 may be embodied in a castable lure 300, the castable lure 300 may include a waterproof housing or body 304 enclosing a sensor assembly 302 within. The castable lure 300 may include one or more hooks, or treble hooks 306, disposed about the body 304 of the castable lure 300, such as at a tail portion and a ventral portion. In some embodiments, the castable lure 300 may include a bill or lip 308 extending from a front or nose 310 of the castable lure. The lip 308 may be configured to cause the castable lure to dive to a predetermined or expected depth, when being reeled in by a fishing line 314 attached to an anchor 312 affixed to bill 308 or nose 310, such as in embodiments which do not include a bill 308. The length and width of the lip 308 and/or weight of the castable lure 300 may determine the predetermined or expected depth at which the castable lure 300 operates. Additionally, the bill 308 and/or the contour of the body 304 may cause the castable lure to deflect side-to-side when being reeled in, or "wobble" as depicted by arrows 316A and 316B in FIG. 3B.

In addition to the length and width of the bill 308 and contour and weight of the body 304, the crack speed applied to the castable lure 300 may also affect the operating depth of the castable lure as well as it wobble. For example, if the castable lure is subjected to an excessively high crank speed, a larger than expected downward force will be applied by the bill 308 causing the castable lure 300 to operate at a depth greater than the expected depth 160 (e.g., FIG. 2C) Similarly, if the castable lure 300 is subjected to an excessively low crank speed, a smaller than expected downward force will be applied by the bill causing the castable lure to operate at a depth less than the expected depth 160 (e.g., FIG. 2B). The wobble 316 of the castable lure 300 may also be affected by the crank speed. For example, the castable lure 300 may wobble excessively at a high crank speed and wobble slightly, or not at all, at low crank speeds.

Figure 3C:
FIG. 3C illustrates an example wobble profile of the crank bait lure in accordance with various implementations described herein.

In an example embodiment, the castable lure 300 may be configured to collect data in addition to depth corresponding to a depth profile 160 and/or wobble profile 316 during each cast (see e.g., the example wobble profile 316 shown in FIG. 3C). The sensor assembly 302 may include a time of flight sensor, such as an accelerometer, gyroscope, gravity switch or the like. The time of flight sensor may measure a change of state or direction of travel of the castable lure, such as when the direction of travel shifts from backward to forward during a cast and sudden deceleration of the castable lure 300 when the castable lure strikes the body of water 102. The sensor assembly may log the time or count of a timer or counter at the first change of state and the time or count at the second change of state and determine, by subtraction, the total time of flight of the castable lure 300. In an example embodiment, a standard distance per time unit may be applied to determine a distance associated with the cast. In some embodiments, acceleration data collected by the accelerometer may be used to determine a distance of the cast. In a further embodiment, angular velocity data collected by the gyroscope may be used in conjunction with the accelerometer data to determine a distance of the cast. The distance determination using accelerometer data and angular velocity data may be similar to the cast profile determination discussed below using the first change of state, e.g. the change to forward travel of the castable lure as the inertial reference frame. In an example embodiment, the depth profile may include a cast distance 164, such as depicted in FIGS. 2A-2C.

As discussed above, data including the pressure data, time of flight data, angular velocity data, acceleration data, environmental condition data, or the like, may be transmitted from the castable device 120 to the computing device for processing. Processing may include, without limitation determining depth profile, three-dimensional cast profile, and fishing recommendations. The data may be transmitted via wired or wireless communication. In an example embodiment, the castable sensor device 120 may be wirelessly paired with the computing device 122, such that when the castable sensor device is proximate to the commuting device 122, such as on the vessel 140, the castable sensor device 120 transmits the data to the computing device 122. When the castable sensor device 122 is not proximate to the computing device 122, such as during a cast, and/or when the castable sensor device is submerged in the body of water 102, the castable sensor device may store the data in a local memory.

Turning first to processing of the environmental data, the computing device 122 may receive the environmental sensor data and pressure data and determine the environmental conditions at various depths and/or along the travel path of the castable sensor device 120. The environmental conditions may be displayed on a user interface in a variety of formats. For example, the environmental conditions may be displayed as text values, as a bar graph, line graph, virtual gages or meters, or the like. In an example embodiment, the environmental condition data may be indicated on the depth profile, such as by color, text or the like.

In an example embodiment, the computing device 122 may receive an indication of one or more fish types. For example, the computing device 122 may receive one or more fish types as a user input from a user interface. In another example, the computing device 122 may determine one or more fish types based on position data. The computing device 122 may determine a position of the vessel 140, e.g. within the body of water 102, and determine one or more fish types associated with the position using a lookup table.

The computing device 122 may be configured to compare the environmental conditions or sensor data to one or more fish profiles to determine if the environmental conditions and/or the travel path of the castable lure are conducive for catching fish. The computing device 122 may compare the environmental condition to one or more fish profiles based on the one or more fishing types. In an example embodiment, the computing device 122 may retrieve one or more fish profiles from a memory based on the one or more fish types. The fish profiles may include one or more environmental conditions or combinations of environmental conditions that are associated with high fish catching rates for the associated fish types. For example, some fish types may prefer deep water, low light, low light intensity, and low chlorophyll when feeding, whereas others prefer shallow water with high oxygen content, high light intensity, and high chlorophyll. Some fish types may have an ideal temperature and oxygen content. The computing device 122 may determine the depth, based on the pressure data, at which the temperature and oxygen content is closest to the ideal temperature and oxygen content of the fish type. In some examples, acidity may be used as a proxy for oxygen content. Low acidity is indicative of low carbon dioxide levels and, thereby, high oxygen content. The level of activity of fish types may be associated with the light intensity as well as the temperature of the surrounding water. For example predator fish generally feed in low light conditions, which may also cause plankton to move higher in a water column. The computing device 122 may determine a depth that has the best water temperature and light intensity for the respective fish types. In addition to determining the ideal fishing depth for one or more fish types, the computing device 122 may also determine the type of presentation, e.g. faster, slower, loader, subtle, etc. for the fish types based on the environmental parameters at one or more depths.

Figure 4A:
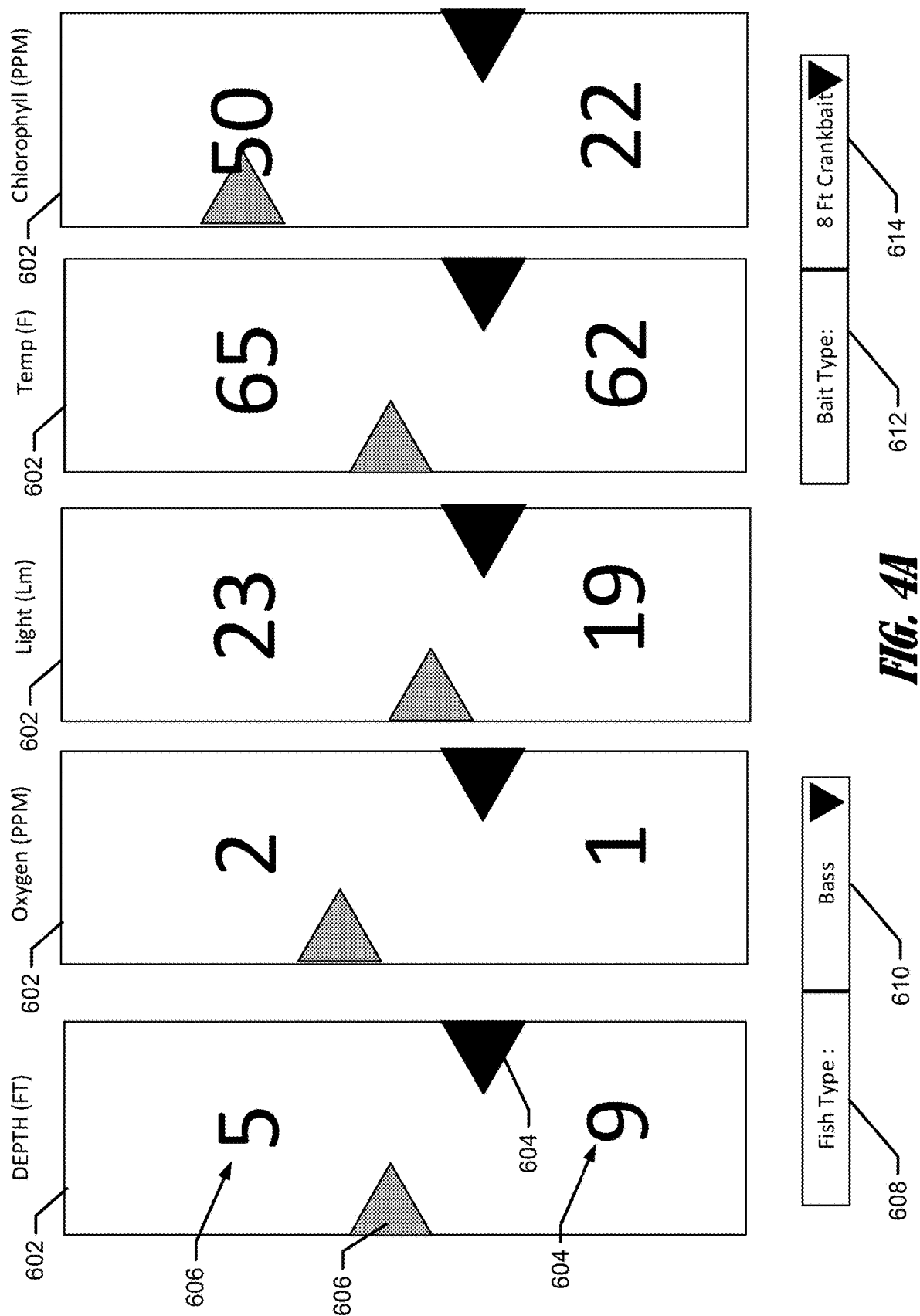
FIG. 4A-4C illustrate example environmental condition displays in accordance with various implementations described herein.

The computing device 122 may display one or more ideal values based on the fish profile and the environmental conditions. As depicted in FIG. 4A, the computing device 122 may display the one or more environmental conditions in text and/or graphic form. In this example, the user interface indicated the environmental conditions displays 602 for depth, oxygen, light intensity, temperature, and chlorophyll. The environmental condition displays 602 may include the ideal value 604, derived from the fish profile and an environmental condition value 606 corresponding to a last cast or an average of casts. In the depicted embodiment, the ideal value 604 and the environmental condition value 606 are depicted both visually, as an arrow comparison, and textually.

As discussed above, the user may provide a user input identifying the fish type 608 using a drop down menu 610, or other suitable user input. Additionally, the user may provide a user input indicating the bait type 612, using a drop down menu 614, or other suitable input. The bait type may be specific to the model of the lure being used, or the expected depth of the lure.

In some example embodiments, the computing device 122 may determine one or more actions based on the comparison of the environmental conditions, e.g. sensor data, to the one or more fish profiles. In an example embodiment, one or more actions may be determined and displayed on a user interface to increase the likelihood of successful fishing casts based on the comparison of the sensor data to the fish profiles. For example, recommending changing of crank speed, lure, bait type, or the like. If the computing device determines that the depth of the lure is lower than the ideal depth for the fish type, the computing device 122 may recommend increasing the crank speed, which may cause the bill of the lure to force the lure deeper in a subsequent cast. Similarly, if lure depth exceeds the ideal depth, the computing device may recommend decreasing crank speed to reduce the downward force provided by the bill of the castable lure during a subsequent cast. In some example embodiments, the computing device 122 may determine a change of castable lure, such as changing from a shallow dive lure to a medium dive lure. In some example embodiments, the computing device 122 may, in addition to or as an alternative to depth based changes, determine a bait type or presentation type, such as based on light intensity or temperature. For example, where the ideal depth is warmer, a louder presentation or more colorful bait may be recommended, where the ideal depth is cooler a more subtle presentation type or subdued color bait may be recommended. In an example embodiment, in which the computing device 122 determines that the environmental conditions are not conducive for catching a fish type, the computing device may recommend changing fish types.

The computing device 122 may be configured to display the one or more actions on the user interface. The actions may be displayed visually or textually, for example an arrow in a particular environmental condition value 602 indicating an increase or decrease of the value, such as depth. In the example depicted in FIG. 4B, a text box 616 or alert box may be provided overlaid on the environmental condition displays 602. Here, the text box 616 indicates the corrective action of 1) increase crank speed to cause the bait to dive deeper" or "2) change bait to a medium diving bait." In the example depicted in FIG. 4C, a text box 616 including recommended actions of "1) use high presentation bait" or "2) use high "wobble bait." In some example embodiments, the computing device 122 may be configured to provide more specific actions, such as a specific rotations per minute of the reel, e.g. crank speed, a particular model of lure or expected dive depth, or a particular type of fish.

Turning to processing of a depth profile and referring to FIGS. 2A-2C, the computing device 122 may receive the pressure data and correlated time stamp data from the castable sensor device 120, as discussed above. The computing device 122 may determine the depth associated with each pressure measurement using a lookup table or applying a conversion ratio, such as EQN. 1.

$$\text{Depth(meters)} = \text{Pressure(decibars)} * 1.019716 \qquad \text{EQN. 1}$$

The computing device 122 may then graph or plot the depth data over time based on the correlated time stamp data. The resulting depth profile 162 may then be displayed on a user interface. In some example embodiments, the computing device may also receive time of flight data from the castable sensor device 120. The computing device 122 may apply a standard distance per time unit to the time of flight data to determine a distance associated with the cast. In some embodiments, acceleration data collected by the accelerometer may be used to determine a distance of the cast. In a further embodiment, angular velocity data collected by the gyroscope may be used in conjunction with the accelerometer data to determine a distance of the cast. The distance determination using accelerometer data and angular velocity data may be similar to the cast profile determination discussed below using the first change of state, e.g. the change to forward travel of the castable lure as the inertial reference frame. In an example embodiment, the depth profile 160 may include a cast distance 164, such as depicted in FIGS. 2A-2C.

The computing device 122 may receive an indication of an expected depth of the castable sensor device 120, such as a user input received from the user interface indicating the expected depth 162. In an example embodiment, user input may include the model or type of castable lure and the computing device 122 may utilize a look up table stored in memory to determine the expected depth 162 associated with the model type of castable lure.

The expected depth 162 may be compared to the depth profile 160 and displayed on the user interface. As depicted in FIG. 2A, the plateau portion of the depth profile 160 is at or near the expected depth 162. However, FIGS. 2B and 2C depict significant deviation of the depth profile 160 from the expected depth 162. Particularly, the castable lure 120 in FIG. 2B has a depth profile substantially shallower than the expected depth and the castable lure 120 in FIG. 2C has a depth profile 2C substantially deeper than the expected depth 162. In some example embodiments, the computing device may determine if the depth profile is within a predetermined range or threshold, such as +/−1 ft., 3 ft., of the like. The computing device 122 may determine a corrective action, in response to the depth profile (e.g., the depth profile plateau) exceeding the predetermined threshold.

Figure 4B:
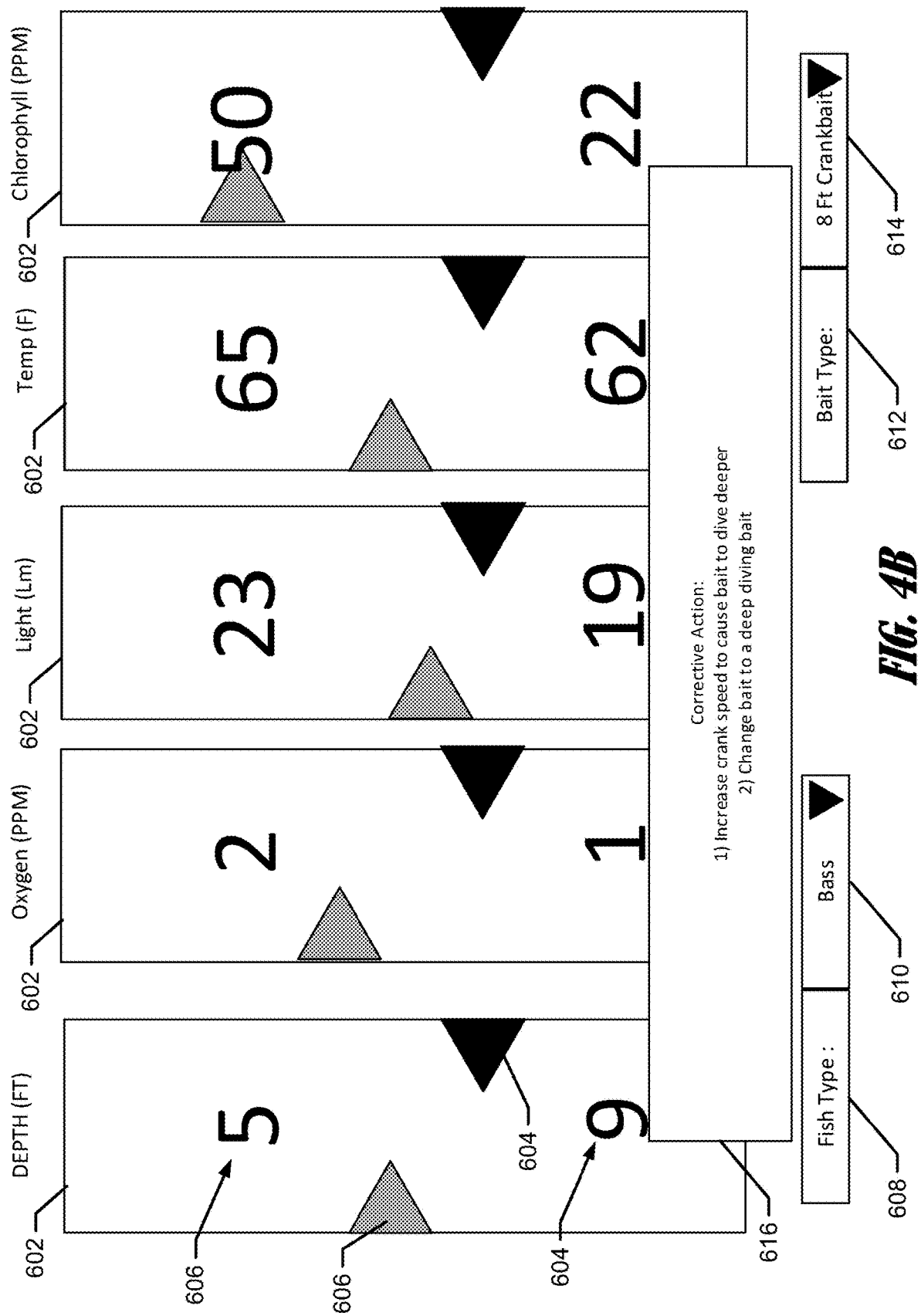
Figure 4C:
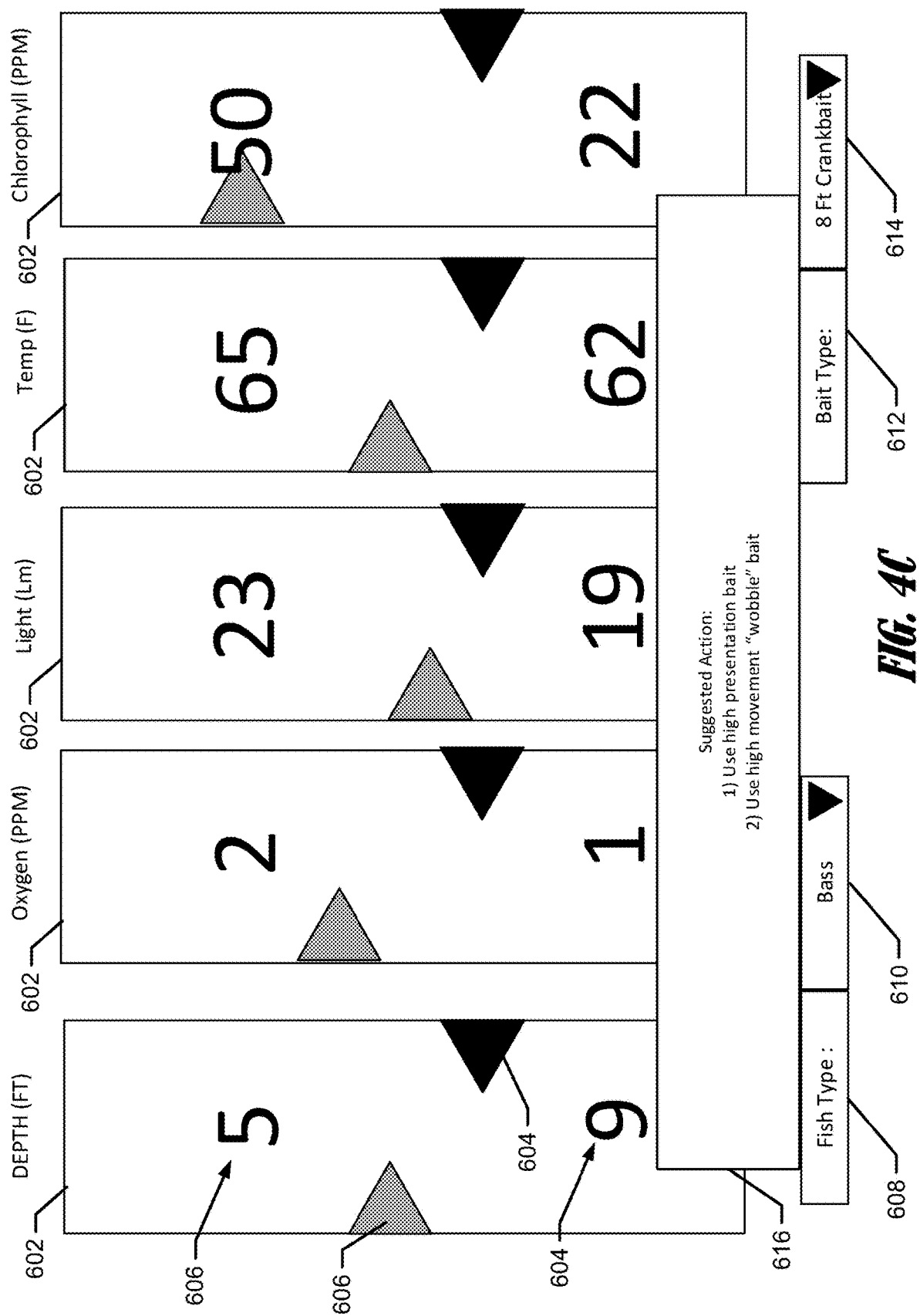

The computing device 122 may determine one or more corrective actions based on the comparison of the depth profile 160 to the expected depth 162, such as recommending increasing the crank speed, which may cause the bill of the lure to force the lure deeper in a subsequent cast. Similarly, if lure depth exceeds the expected depth, the computing device may recommend decreasing crank speed to reduce the downward force provided by the bill of the castable lure during a subsequent cast. The corrective action may be displayed on the user interface, such as depicted in FIG. 4B and described above.

Turning to processing of the three-dimensional cast profile, the computing device 122 may receive the angular velocity data and acceleration data with correlated time stamp data from the castable sensor device 120. The computing device 122 may determine orientation data based on an angular velocity measured by the gyroscope associated with the castable sensor device. The orientation data may include a yaw angle, a pitch angle, and a roll angle. The accelerometer data may be associated with accelerometers associated with each of a yaw axis, a pitch axis, and a roll axis configured to measure the linear acceleration associated with each axis. The computing device 122 may set an inertial reference frame based on the orientation data. The deviations from the inertial reference frame may be indicative of movement of the gyroscope, and thereby movement of the castable sensor device 122. The inertial reference frame may be set based on data corresponding to a change of state of one or more of the accelerometers indicating rapid decreased in forward motion indicative of the castable sensor device 120 striking the water during a cast. The computing device 122 may calculate a current inertial position for each set of angular velocity data and acceleration data received after the inertial reference frame is set, as discussed below. A plot of each of the current inertial positions renders a three-dimensional cast profile including both a depth profile and a wobble profile. The computing device 122 may determine linear accelerations in the inertial reference frame based on the acceleration data and the angular velocity data. The computing device 122 may determine the orientation of each axis of the inertial reference frame and the linear acceleration associated with each axis. The computing device 122 may determine inertial velocities based on the linear acceleration. To reduce error or drift in orientation, the computing device 122 may receive magnetic field strength data from a magnetometer associated with the castable sensor device 120. The computing device 122 may utilize the magnetic field strength data to determine a heading angle. The heading angle may be used to correct orientation drift or error in the calculated orientation of the gyroscope. The computing device 122 may integrate the linear velocities using kinematics equations to determine a current velocity of the castable sensor device for each data set. The computing device 122 may then integrate the computed current velocity to determine a current inertial position relative to an initial position set by the inertial reference frame. The computing device may then plot each of the current inertial positions associated with each data set to render a three-dimensional cast profile for the castable sensor device 122 including both a depth profile and a wobble profile.

The computing device 122 may be receive an indication of an expected depth and expected wobble profile. The expected depth and wobble profile may be received in a manner substantially similar to receiving the expected depth, as discussed above.

The computing device 122 may compare the three-dimensional cast profile to the expected depth and expected wobble profile and display the comparison on a user interface. The depth profile to expected depth comparison of the three-dimensional cast profile may be substantially similar to the depth profile to expected depth comparison, as discussed above. The computing device 122 may determine if the deviation to the left and right of the travel path of the castable sensor device 120 and/or the left and right deviation of the castable sensor device 120 about a vertical axis (318 FIG. 3A) of the castable sensor device 120 is within a predetermined range or threshold, such as +/−1 in travel deflection and/or 1 axial deflection per second. The computing device 122 may determine a corrective action, in response to the travel deflection or axial deflection exceeding the predetermined threshold. For example, the computing device 122 may determine a slower crank speed to increase travel deflection and decrease axial deflection. The computing device 122 may determine a faster crank speed to decrease travel deflection and increase axial deflection. The corrective action may be displayed on the user interface, such as in a text box or other suitable display.

In some example embodiments, the computing device 122 may cause the depth profile, three dimensional cast profile, and an indication of the expected depth or expected wobble profile to be transmitted to a network server, such as a manufacturer's server for product feedback and development. In an example embodiment, the computing device 122 may be a manufacturer's device and perform the steps discussed below. The network server may receive the depth profile, three dimensional cast profile, and an indication of the expected depth and/or expected wobble profile and perform a comparison of the depth profile to the expected depth profile and/or the three dimensional cast profile to the expected depth and expected wobble profile, which may be substantially similar to the comparisons discussed above. The network server may then determine one or more modifications to the castable sensor device based on the comparison. For example, the network server may increase the length of the bill 308 if the castable sensor device 120 is not reaching the expected depth to increase the downward force applied to the castable sensor device 120 when being reeled in. Similarly, the network server may decrease the length of the bill to reduce the depth profile of the castable sensor device 120. In an example embodiment, the network server may determine a change to the width of the bill 308, a change to the weight or distribution of weight in the body of the castable sensor device 120, and/or a change to the contour of the body of the castable sensor device 120. In some example embodiments, the network device may cause one or more of the modifications to be implemented in a model of the castable sensor device 120. In an example embodiment, the network device may cause a manufacturing device to generate a castable sensor device based on the model and/or the modifications.

In some example embodiments, the castable sensor device 120 may include a sonar transducer or be associated with a sonar transducer. The sonar transducer may be configured to emit a sonar signal into the body of water 102 when the castable sensor device 120 is at least partially submerged. In an example embodiment, the sonar transducer may be utilized to transmit the data, including but not limited to pressure data, time of flight data, angular velocity data, acceleration data, environmental condition data, and the like, from the castable sensor device to the computing device 122. In one such embodiment, the data may be transmitted to the computing device using underwater acoustic communications (UAC) on the sonar signal.

Figure 5:
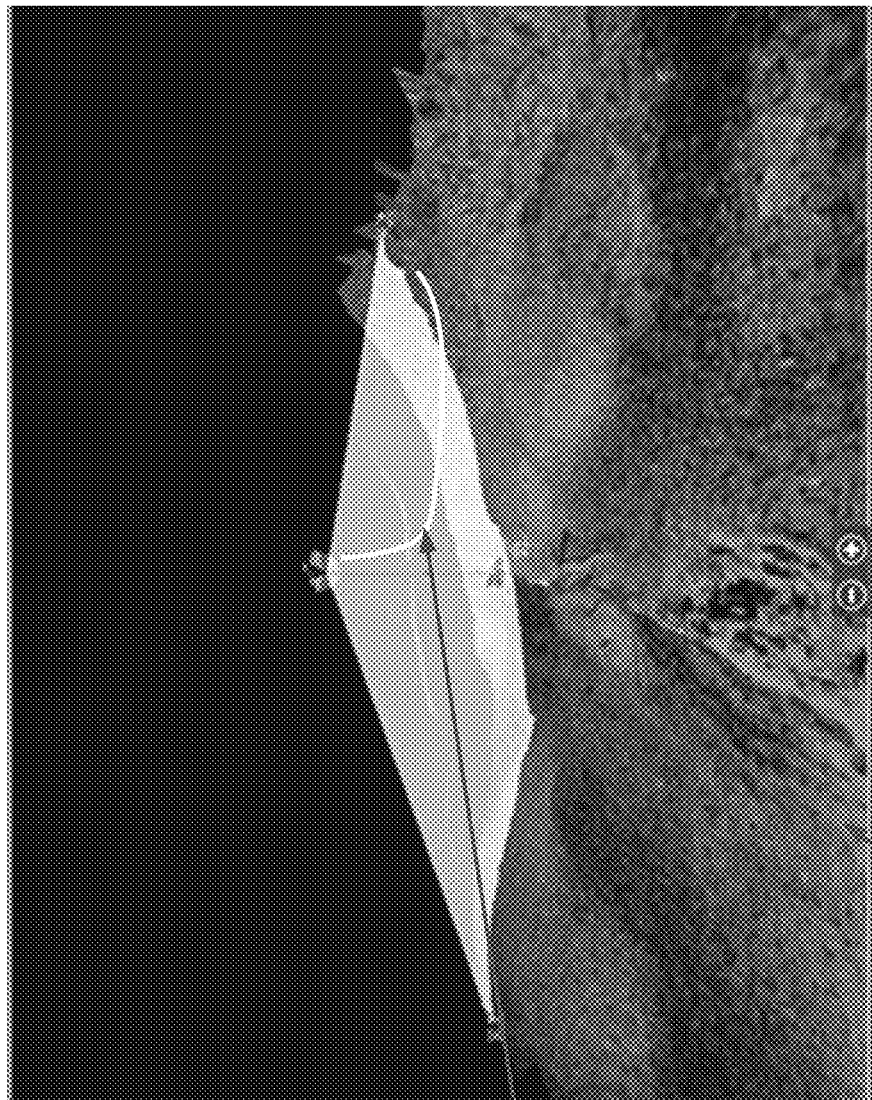
FIG. 5 illustrates an example sonar image including a sonar cast profile in accordance with various implementations described herein.

The computing device 122 may receive the sonar signal using a sonar transducer or a dedicated UAC receiver. The computing device 122 may receive the sonar signal as a portion of a sonar return and generate a sonar image. The computing device 122 may plot the sonar signal in the sonar image and display the sonar image on a user interface providing real time tracking of the castable sensor device 120 in the body of water 102. In an example embodiment, the computing device 122 may plot the location of the sonar signal in the sonar image 502 from a plurality of sonar returns, such that the plurality of sonar signal plots renders a sonar cast profile 504, which may be displayed on the user interface, such as depicted in FIG. 5. The sonar cast profile 504 may be utilized as a real time representation of the travel path of the castable sensor device enabling the user to dynamically adjust crank speed to adjust the depth and wobble of the castable sensor device 120. Additionally or alternatively, the sonar cast profile may be compared to an expected depth profile and/or expected wobble profile similar to the three dimensional cast profile, as discussed above.

Figure 6A:
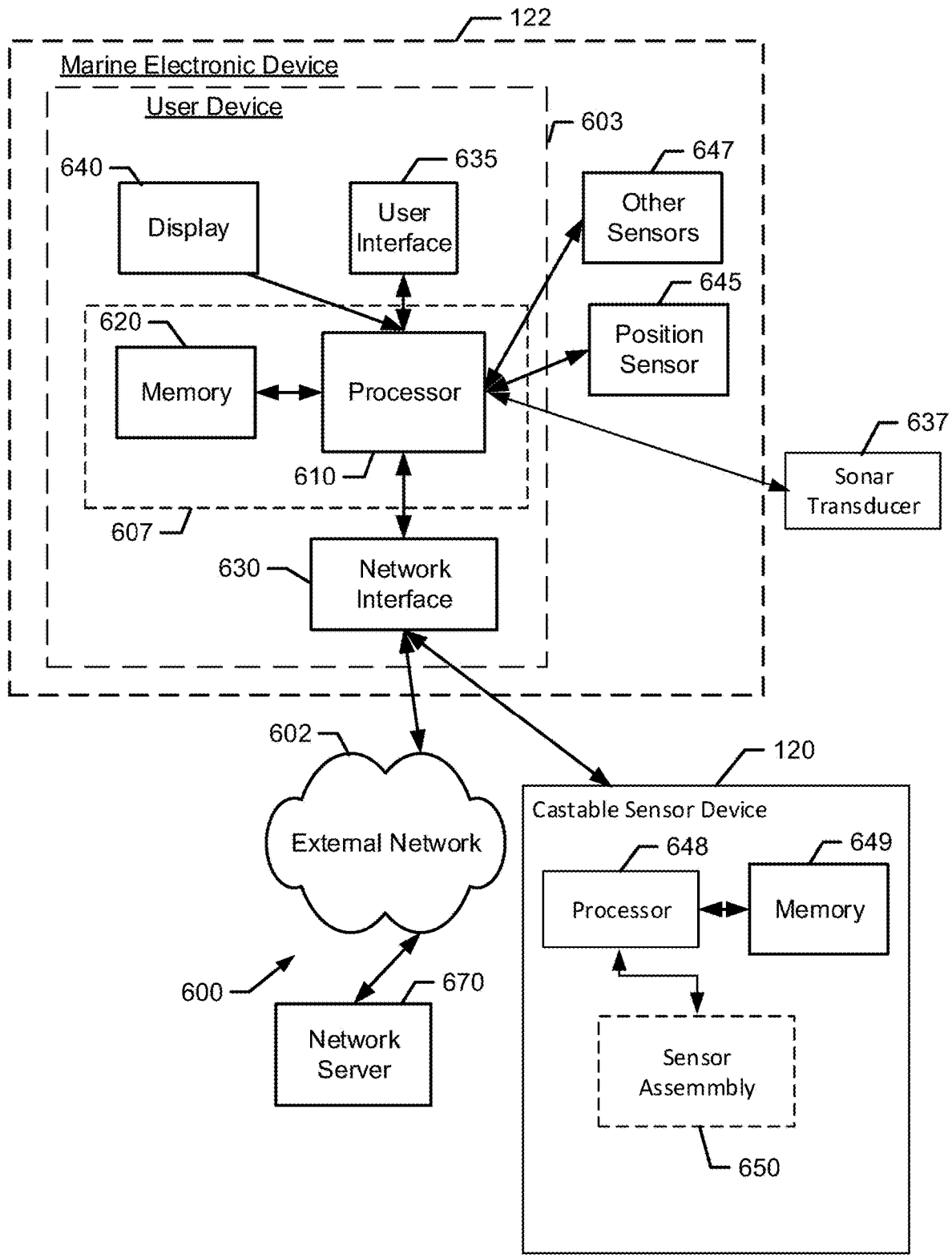
FIGS. 6A-6B illustrate various diagrams of sensor systems in accordance with various implementations described herein.
Figure 6B:
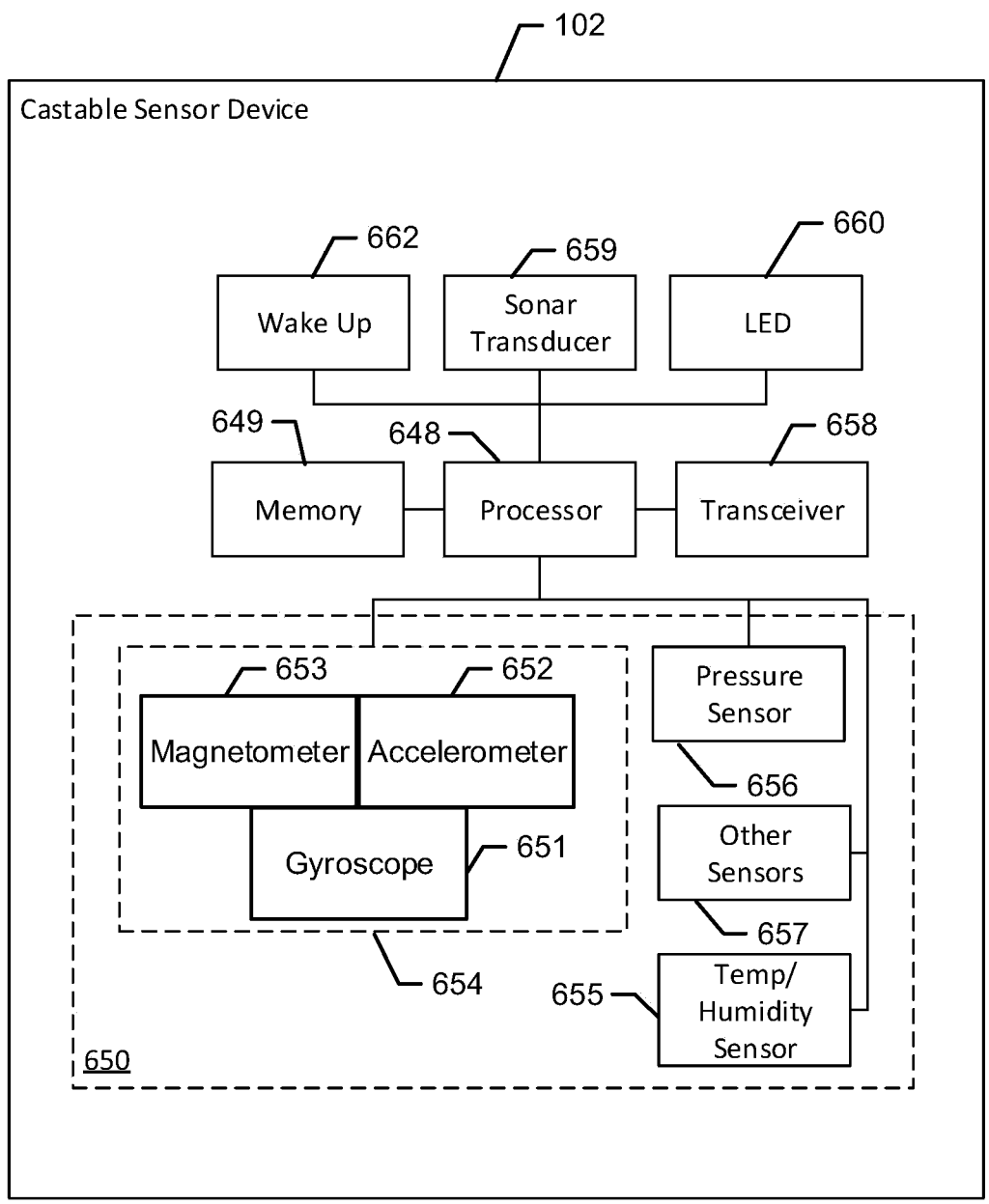

FIGS. 6A-6B illustrate example block diagrams of a sensor system 600 in accordance with various implementations described herein. In particular, FIG. 6A illustrates a diagram of the sensor system 600 using a castable sensor device 120 with at least one environmental sensor 210, and FIG. 6B illustrates a diagram of the castable device 120 with a sensor assembly 650 having multiple environmental sensors 651-657 (shown in FIG. 6B). In various implementations, the sensor assembly 650 may include any number of environmental sensors 650-657, including one, two, or more than two environmental sensors.

In reference to FIG. 6A, the sensor system 600 may include the castable device 120 having the at least one environmental sensor, included in a sensor assembly 650, a computing device 122, such as a marine electronic device, and a network server 670. In some implementations, the castable device 120 may be configured to generate and transmit sensor data to the computing device 122 via a wired or wireless network, and the computing device 122 may be configured to transmit or upload the sensor data received from the castable device 120 to the network server 670 via a wired or wireless network.

Referring to both FIGS. 6A and 6B, the castable device 120 may include a sensor assembly 650 including the at least one environmental sensor 651-657, at least one processor 648, memory 649, and a network interface. The at least one environmental sensor 651-657 may be configured to generate sensor data at one or more depths of the castable device 120 in water (e.g., body of water 102) and/or during a cast. The at least one environmental sensor 210 may be configured to detect levels of environmental content, concentrations, and/or characteristics of water at a surface and/or at various depths beneath the surface. For instance, the detectable environmental characteristics may include one or more of pressure (e.g., atmospheric pressure, water pressure, etc.), chlorophyll concentration, oxygen concentration, temperature, light intensity, electrolyte concentration (e.g., salt content), acidity, etc.

The castable device 120 may include the processor 648 and the memory 649 having instructions that cause the processor 648 to receive sensor data from the at least one environmental sensor 651-657 and record the sensor data received from the at least one environmental sensor at one or more depths (e.g., at a surface and/or during vertical movement) of the castable device 120 in a column of water or during a cast. In some instances, vertical movement refers to ascent and/or descent of the castable device 120 in a column of water. In some other instances, sensor data may be generated by the at least one environmental sensor 651-657 and recorded while the castable device 120 is holding or remains stationary in a column of water. In yet further instances, the sensor data may be generated during substantially horizontal movement toward the vessel 140 (FIG. 1), such as while the castable device is being reeled in during a cast.

The processor 648 may be any means configured to execute various programmed operations or instructions stored in a memory device such as a device or circuitry operating in accordance with software or otherwise embodied in hardware or a combination of hardware and software (e.g. a processor operating under software control or the processor embodied as an application specific integrated circuit (ASIC) or field programmable gate array (FPGA) specifically configured to perform the operations described herein, or a combination thereof) thereby configuring the device or circuitry to perform the corresponding functions of the processor 648 as described herein. In this regard, the processor 648 may be configured to analyze electrical signals communicated thereto to provide or receive sensor data.

In an example embodiment, the memory 649 may include one or more non-transitory storage or memory devices such as, for example, volatile and/or non-volatile memory that may be either fixed or removable. The memory 649 may be configured to store instructions, computer program code, marine data, such as sonar data, chart data, location/position data, and other data associated with the navigation system in a non-transitory computer readable medium for use, such as by the processor 648 for enabling the castable device 120 to carry out various functions in accordance with example embodiments of the present invention. For example, the memory 469 could be configured to buffer input data for processing by the processor 648. Additionally or alternatively, the memory 649 could be configured to store instructions for execution by the processor 648.

The castable device 120 may include the network interface, and the memory 649 may include instructions that cause the processor 648 to transmit sensor data generated by the at least one environmental sensor 650-657 and/or recorded by processor 648. In some instances, the network interface may include a transmitter or transceiver 658 configured to transmit sensor data to the computing device 122, such as, e.g., a marine electronics device, multi-function display (MFD), smart phone, computer, laptop, tablet, etc. In various instances, transmission of sensor data between the castable device 120 and the computing device 122 may occur via a wired or wireless network. Further, in some instances, transmission of sensor data between the castable device 120 and the computing device 122 may occur when the castable device 120 surfaces from water. Further, in some instances, transmission of sensor data may occur in response to detecting a network, such as a wired or wireless network, e.g. a Bluetooth or NFC network. In some other instances, transmission of sensor data between the castable device 120 and the computing device 122 may occur while the castable device 120 is submerged in water via an underwater wired or wireless channel.

In some implementations, the castable device 120 may be configured to transmit sensor data to the computing device 122 through the body of water 102 with water as a transmission channel or medium for wireless communication between the castable device 120 and the computing device 122. Therefore, the network interface of the castable device 120 may include a sonar transducer configured to transmit sensor data to the network interface of the computing device 120 through the body of water 102 with water as a transmission channel or medium for wireless communication between the castable device 120 and the computing device 122, such as by using underwater acoustic communications (UAC). The sonar transducer 659 may transmit a sonar signal including the sensor data into the body of water. The computing device 122 may receive the sonar signal and sensor data via a sonar transducer 637 or dedicated UAC receiver.

In various implementations, the castable device 120 may be deployed in water (e.g., in the body of water 102), which may include casting the castable device 120 in water by a user. Therefore, the castable device 120 may include a waterproof housing that is impervious to water. In some instances, the castable device 120 may include a castable lure or fishing bait. Further, in some instances, the at least one environmental sensor 651-657 and other components of the castable device 120 may be encapsulated within the waterproof housing for protection from water damage.

The castable device 120 may include a wakeup button or switch 662 configured to selectively provide power to the processor 648 and other components of the castable device 120. The castable device 120 may also include one or more indicators, such as light emitting diodes 660, configured to provide an indication of a power status of the castable device 120 and/or one or more operating modes.

In an example embodiment, the sensor assembly 650 may include a gyroscope 651, an accelerometer 652, and/or a magnetometer 653. The gyroscope 651, the accelerometer 652, and/or the magnetometer 653 may be portions of a microelectromechanical system (MEMS) 654. The gyroscope 651 may be configured to measure an angular velocity of the gyroscope 651. In some example embodiments, the gyroscope 651 may be a vibrating structure MEMS gyroscope including gyroscopic sensors oriented in a plurality of axes. The accelerometer 652 may be configured to measure acceleration of the accelerometer. In some example embodiments, the accelerometer may be a variable capacitive (VC) MEMS accelerometer, a piezoresistive (PR) MEMS accelerometer, or the like. The magnetometer 653 may be configured to measure a magnetic field strength, which may be used to find magnetic north and/or a heading angle. In an example embodiment, the magnetometer may be a Lorentz force based MEMS sensor, electron tunneling MEMS sensor, MEMS compass, or the like.

The pressure sensor 656 may be a piezoresistive pressure sensor configured to measure a water pressure applied to the castable device 120 when deployed in the body of water 102. In one such example the pressure sensor 656 may be disposed proximate to or in contact with the housing, such that the pressure sensor 656 measures the water pressure applied to the housing, which may be correlated to a water depth by the processor 648 and/or the computing device 122 by comparing the pressure measurement, e.g., pressure data to a lookup table or applying a conversion ratio, such as EQN. 1.

In some example embodiments, the castable device 120 may also include a temperature sensor 655. The temperature sensor 655 may be a digital temperature sensor, such as a silicon band gap sensor or other suitable temperature sensor configured to measure the temperature of the body of water 102. The temperature sensor 655 may be disposed proximate to or in contact with the housing, such that the temperature sensor measures the temperature of the water surrounding the castable device 120. In some instances the temperature sensor 655 may also be configured to measure a humidity proximate to the castable device 120.

As discussed above, the sensor assembly 650 may include one or more other sensors 657 configured to measure one or more additional environmental parameters of the body of water 102 while the castable device is at least partially submerged. The other sensors may include, without limitation, a chlorophyll sensor, an oxygen sensor, a temperature sensor, a light sensor, an electrolyte sensor, or an acidity sensor.

In some implementations, the computing device 122 may be configured to receive sensor data from the castable device 120 over a wired or wireless network via a network interface 630. The computing device 122 may include a processor 610 and memory 620 having instructions that cause the processor 610 to process the sensor data and/or generate display images associated with the sensor data on a display component or device 640 and/or user interface 635. Further, the computing device 122 may be configured to create/generate sensor data logs associated with the sensor data. The computing device 122 may be configured to store, record, and/or log the sensor data and/or sensor data logs in one or more databases (e.g., memory 620). Further, the computing device 122 may be configured to upload the sensor data and/or sonar logs to the network server 670 connected to an external network 602, such as, e.g., a cloud server or other network server, via the network interface 630.

The processor 610 may be any means configured to execute various programmed operations or instructions stored in a memory device such as a device or circuitry operating in accordance with software or otherwise embodied in hardware or a combination of hardware and software (e.g. a processor operating under software control or the processor embodied as an application specific integrated circuit (ASIC) or field programmable gate array (FPGA) specifically configured to perform the operations described herein, or a combination thereof) thereby configuring the device or circuitry to perform the corresponding functions of the processor 610 as described herein. In this regard, the processor 610 may be configured to analyze electrical signals communicated thereto to provide or receive sonar data, sensor data, position data, and/or additional environmental data. For example, the processor 610 may be configured to receive sonar return data, generate sonar image data, generate one or more sonar images based on the sonar image data, analyze sensor data, and generate one or more sensor data displays based on the sensor data.

In an example embodiment, the memory 620 may include one or more non-transitory storage or memory devices such as, for example, volatile and/or non-volatile memory that may be either fixed or removable. The memory 620 may be configured to store instructions, computer program code, marine data, such as sonar data, chart data, location/position data, and other data associated with the navigation system in a non-transitory computer readable medium for use, such as by the processor 610 for enabling the computing device 122 to carry out various functions in accordance with example embodiments of the present invention. For example, the memory 620 could be configured to buffer input data for processing by the processor 620. Additionally or alternatively, the memory 620 could be configured to store instructions for execution by the processor 610.

The network interface 630 may be configured to enable connection to external systems (e.g. an external network 602). In this manner, the computing device 122 may retrieve stored data from a network server 670 via the external network 602 in addition to or as an alternative to the onboard memory 620. Additionally or alternatively, the computing device 122 may transmit or receive data, such as sensor data to or from a castable device 120, more particularly to or from a processor 649.

The display 640, e.g. screen, may be configured to display images and may include or otherwise be in communication with a user interface 635 configured to receive input from a user. The display 640 may be, for example, a conventional LCD (liquid crystal display), a touch screen display, mobile device, or any other suitable display known in the art upon which images may be displayed.

In any of the embodiments, the display 640 may present one or more sets of marine data (or images generated from the one or more sets of data). Such marine data includes chart data, radar data, weather data, location data, position data, orientation data, sonar data, or any other type of information relevant to the watercraft. In some embodiments, the display 640 may be configured to present such marine data simultaneously as one or more layers or in split-screen mode. In some embodiments, a user may select any of the possible combinations of the marine data for display.

In some further embodiments, various sets of data, referred to above, may be superimposed or overlaid onto one another. For example, a route may be applied to (or overlaid onto) a chart (e.g. a map or navigational chart). Additionally or alternatively, depth information, weather information, radar information, sonar information, or any other navigation system inputs may be applied to one another.

The user interface 635 may include, for example, a keyboard, keypad, function keys, mouse, scrolling device, input/output ports, touch screen, or any other mechanism by which a user may interface with the system.

Although the display 640 of FIG. 6A is shown as being directly connected to the processor 610 and within the computing device 122, the display 640 could alternatively be remote from the processor 610 and/or computing device 122. Likewise, in some embodiments, the position sensor 645 and/or user interface 635 could be remote from the computing device 122.

The computing device 122 may also include a position sensor 645 that may be configured to determine the current location of the computing device 122. For example, the position sensor 645 may comprise a GPS, bottom contour, or other location detection system.

The computing device 122 may include one or more other sensors 647 configured to measure environmental conditions. The other sensors 647 may include, for example, an air temperature sensor, a water temperature sensor, a current sensor, a light sensor, a wind sensor, a speed sensor, or the like.

In some implementations, the computing device 122 may be configured to store and record multiple sensor data logs and create/generate one or more sensor data maps of a body of water 102 therefrom. For instance, the computing device 122 may be configured to create/generate one or more maps by stitching, combining, and/or joining multiple sensor data logs together. Further, in some instances, the computing device 122 may be configured to receive geo-coordinate data, such as global positioning system data (i.e., GPS data), via the position sensor 645, such as a GPS transceiver and associate the received GPS data to the sensor data, sensor data logs, and/or sensor data maps at any time, including prior to upload to the network server 290.

In various implementations, the computing device 122 may be configured as a special purpose machine for interfacing with a castable device 122 having at least one environmental sensor 650-657. Further, the computing device 122 may include various standard elements and/or components, including the at least one processor 610, the memory 620 (e.g., non-transitory computer-readable storage medium), at least one database, power, peripherals, and various other computing components that may not be specifically shown in FIG. 6A. The user interface 635 may be used to receive one or more preferences from a user of the display device 640 for managing or utilizing the sensor system 600, including interfacing with the castable device 120 and the one or more environmental sensors 650-657. As such, a user may setup desired behavior of the sensor system 600 and/or the one or more environmental sensors 651-657 via user-selected preferences using the user interface 634 associated with the display device 640. Various elements and/or components of the system 600 that may be useful for the purpose of implementing the system 600 may be added, included, and/or interchanged, in manner as described herein.

Further, in various implementations, each of the environmental sensors 651-657 may be configured to periodically generate environmental sensor data at pre-determined time intervals and/or at pre-determined depth intervals. For instance, the pre-determined time intervals may refer to generating environmental sensor data for each unit of time, such as, e.g., seconds, minutes, etc. As such, the processor 648 may include or be in communication with a clock, counter, or the like configured to provide a measure of unit time. In another instance, the pre-determined depth intervals may refer to generating environmental sensor data for each unit of depth, such as, e.g., inches, feet, meters, etc. In some other instances, the pre-determined depth intervals may refer to generating sensor data for each unit of change in water pressure, such as, e.g., Pascal's, psi, bars, atmospheres, etc.

In various implementations, at least one of the environmental sensors 651-657 may include the pressure sensor 656 configured to detect, determine, and/or identify pressure at one or more depths of the castable device 120 in water (e.g., a column of water in the body of water 102). The pressure sensor 656 may be configured to generate sensor data including pressure data corresponding to depth data at the one or more depths of the castable device 120. The pressure sensor 656 may be configured to detect, determine, and/or identify one or more of atmospheric pressure, barometric pressure, water pressure, etc. In some instances, the pressure sensor data may be received and/or recorded at a surface of a column of water. In some instances, the pressure sensor data may be received and/or recorded at one or more depths during vertical movement (e.g., ascent and/or descent) of the castable device 120 in a column of water. In some other instances, the pressure sensor data may be received and/or recorded at one or more depths while the castable device 120 is holding or remains stationary in the column of water.

In some instances, fish may become more or less active when water pressure drops or rises. Thus, an environmental sensor that detects pressure in the atmosphere, as well as under the water surface, may assist anglers and fishermen with detecting pressure changes to determine when fish may be more or less active. Therefore, the castable device 120 with one or more environmental sensors 651-657 may assist anglers and fishermen with targeting and learning when and where fish are more or less active to possibly reduce unproductive fishing times.

In various implementations, at least one of the environmental sensors 651-657 may include a chlorophyll sensor configured to detect, determine, and/or identify chlorophyll concentration at one or more depths of the castable device 120 in a column of water or during a cast. Further, the chlorophyll sensor may be configured to generate sensor data including chlorophyll concentration data corresponding to depth data at the one or more depths of the castable device 120. In some instances, the chlorophyll sensor data may be received and/or recorded at a surface of a column of water. In some instances, the chlorophyll sensor data may be received and/or recorded at one or more depths during vertical movement (e.g., ascent and/or descent) of the castable device 120 in a column of water. In some other instances, the chlorophyll sensor data may be received and/or recorded at one or more depths while the castable device 120 is holding or remains stationary in the column of water. Additionally or alternatively, the chlorophyll sensor data may be received and/or recorded at in the travel path of the castable device 120 during a cast.

In some instances, smaller bait fish tend to feed on chlorophyll immersed in water, and larger bait fish tend to follow the smaller bait fish around hoping to feed off of them. Larger game fish tend to feed off of the larger bait fish. In these instances, a chlorophyll sensor may assist anglers and fisherman in locating and finding where bait fish may be gathering, and a chlorophyll sensor may assist anglers and fisherman with either catching bait for use on game fish or catching game fish in an area where the chlorophyll is gathering or has gathered. Therefore, the castable device 120 with one or more environmental sensors 651-657 may assist anglers and fishermen with targeting and learning when and where small bait fish may be gathering.

In various implementations, at least one of the environmental sensors 651-657 may include an oxygen sensor configured to detect, determine, and/or identify oxygen concentration at one or more depths of the castable device 120 in a column of water. Further, the oxygen sensor may be configured to generate sensor data including oxygen concentration data corresponding to depth data at the one or more depths of the castable device 120. In some instances, the oxygen sensor data may be received and/or recorded at a surface of a column of water. In some other instances, the oxygen sensor data may be received and/or recorded at one or more depths during vertical movement (e.g., ascent and/or descent) of the castable device 120 in a column of water. In still some other instances, the oxygen sensor data may be received and/or recorded at one or more depths while the castable device 120 is holding or remains stationary in the column of water. Additionally or alternatively, the oxygen sensor data may be received and/or recorded at in the travel path of the castable device 120 during a cast.

In some instances, fish may become inactive and lethargic in water columns having low oxygen levels. In these instances, searching for higher levels of oxygen in various water columns may assist anglers and fishermen with detecting active fish and productive water depths for fishing. Therefore, the castable device 120 with one or more environmental sensors 650-657 may assist anglers and fishermen with targeting highly oxygenated waters to possibly increase fishing productivity.

In various implementations, at least one of the environmental sensors may include the temperature sensor 655 configured to detect, determine, and/or identify temperature at one or more depths of the castable device 120 in a column of water. Further, the temperature sensor 655 may be configured to generate sensor data including temperature data corresponding to depth data at the one or more depths of the castable device 120. In some instances, the temperature sensor data may be received and/or recorded at a surface of a column of water. In other instances, the temperature sensor data may be received and/or recorded at one or more depths during vertical movement (e.g., ascent and/or descent) of the castable device 120 in a column of water. In some other instances, the temperature sensor data may be received and/or recorded at one or more depths while the castable device 120 is holding or remains stationary in the column of water. Additionally or alternatively, the temperature sensor data may be received and/or recorded at in the travel path of the castable device 120 during a cast.

In some instances, fish may seek out and hold in water columns at particular temperature levels, e.g., particularly in temperature breaks where water temperature may rapidly change. In these instances, searching for these temperature breaks may assist anglers and fishermen with detecting active fish and productive water depths for fishing. Therefore, the castable device 120 with one or more environmental sensors 651-657 may assist anglers and fishermen with targeting different temperature zones to possibly increase fishing productivity.

In various implementations, at least one of the environmental sensors 650-657 may include a light sensor configured to detect, determine, and/or identify light intensity at one or more depths of the castable device 120 in a column of water. Further, the light sensor may be configured to generate sensor data including light intensity data corresponding to depth data at the one or more depths of the castable device 120. In some instances, the light intensity sensor data may be received and/or recorded at a surface of a column of water. In other instances, the light intensity sensor data may be received and/or recorded at one or more depths during vertical movement (e.g., ascent and/or descent) of the castable device 120 in a column of water. In some other instances, the light intensity sensor data may be received and/or recorded at one or more depths while the castable device 120 is holding or remains stationary in the column of water. Additionally or alternatively, the light sensor data may be received and/or recorded at in the travel path of the castable device 120 during a cast.

In various implementations, at least one of the environmental sensors 651-657 may include an electrolyte sensor configured to detect, determine, and/or identify electrolyte concentration at one or more depths of the castable device 120 in a column of water. Further, the electrolyte sensor may be configured to generate sensor data including electrolyte concentration data corresponding to depth data at the one or more depths of the castable device 120. In some instances, the electrolyte sensor data may be received and/or recorded at a surface of a column of water. In other instances, the electrolyte sensor data may be received and/or recorded at one or more depths during vertical movement (e.g., ascent and/or descent) of the castable device 120 in a column of water. In some other instances, the electrolyte sensor data may be received and/or recorded at one or more depths while the castable device 120 is holding or remains stationary in the column of water. Additionally or alternatively, the electrolyte sensor data may be received and/or recorded at in the travel path of the castable device 120 during a cast.

In various implementations, at least one of the environmental sensors 651-657 may include an acidity sensor configured to detect, determine, and/or identify acidity or acid concentration at one or more depths of the castable device 120 in a column of water. Further, the acidity sensor may be configured to generate sensor data including acidity or acid concentration data corresponding to depth data at the one or more depths of the castable device 120. In some instances, the acidity sensor data may be received and/or recorded at a surface of a column of water. In other instances, the acidity sensor data may be received and/or recorded at one or more depths during vertical movement (e.g., ascent and/or descent) of the castable device 120 in a column of water. In still some other instances, the acidity sensor data may be received and/or recorded at one or more depths while the castable device 120 is holding or remains stationary in the column of water. Additionally or alternatively, the acidity sensor data may be received and/or recorded at in the travel path of the castable device 120 during a cast.

In various implementations, the one or more environmental sensors 651-657 may include a water sensor. Therefore, in some instances, the castable device 120 may include electrode terminals as part of a water sensor configured to activate the castable device 120 when the castable device 120 is deployed in water (e.g., the body of water 102). In this instance, the water sensor may be configured for automatically sensing deployment of the castable device 120 in water, which may occur after casting the castable device 120 in water by a user. Further, the electrode terminals of the water sensor may be configured to deactivate the castable device 120 when the castable device 120 is removed from water. In some instances, the memory instructions may be configured to cause the processor to transmit sensor data in response to the castable device 120 surfacing from water or detecting removal from water. In other instances, the water sensor may be configured to automatically detect or sense removal of the castable device 120 from water, which may occur after reeling in the castable device 120 out of water by a user.

Embodiments of the present invention provide methods, apparatus and computer program products for operating a marine system, such as described herein. Various examples of the operations performed in accordance with embodiments of the present invention will now be provided with reference to FIGS. 7-11.

Figure 7:
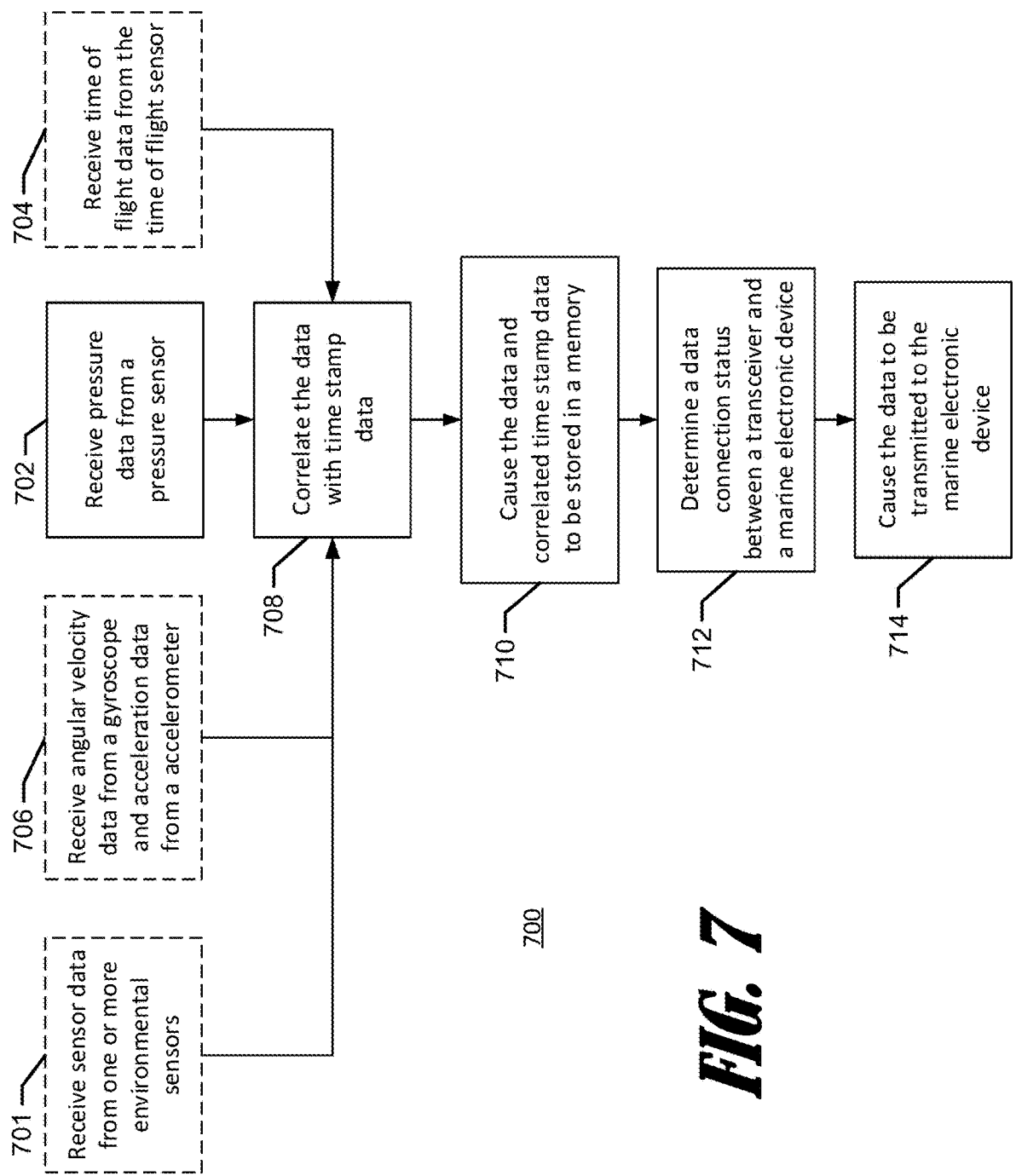
FIGS. 7-11 illustrate example process flows of methods for using a castable sensor device in accordance with various implementations described herein.

FIG. 7 illustrates a process flow diagram for a method 700 performed by a castable sensor device in accordance with implementations of techniques described herein. It should be understood that while method 700 indicates a particular order of execution of operations, in some instances, certain portions of the operations may be executed in a different order, and on different systems. Further, in some other instances, additional operations or steps may be added to method 700. Similarly, some operations or steps may be omitted, as indicated by dashed lines.

At block 701, method 700 may receive sensor data from one or more environmental sensors. For instance, method 700 may be performed by a castable sensor device, which includes one or more environmental sensors configured to generate sensor data at one or more depths of the device in a column of water. As described herein, the one or more environmental sensors may be configured to detect, determine, and/or identify levels of environmental content, concentrations, and/or characteristics of the column of water at a surface and/or at various depths beneath the surface. In various instances, the environmental sensors may be configured to generate sensor data related to depth, pressure, chlorophyll concentration, oxygen concentration, temperature, light intensity, electrolyte concentration (e.g., salt content), acidity, etc.

At block 702, the method 700 may receive pressure data from the pressure sensor. The pressure data may be received at one or more depths in the water column or during a cast of the castable sensor device.

At block 704, method 700 may receive time of flight data from a time of flight sensor. At block 706, method 700 may receive angular velocity data from a gyroscope and acceleration data from an accelerometer. Method 700 may correlate the data with time stamp data at block 708.

At block 710, method 700 may cause the data and the correlated time stamp data to be stored in a memory. For instance, method 700 may store, record, and/or log sensor related data generated by one or more environmental sensors at various depths in a column of water.

At block 712, method 700 may determine a data connection status between the transceiver and the marine electronic device. The data connection status may be a wired or wireless data connection between the castable sensor device and the computing device, such as a Bluetooth, BLE, or NFC connection.

At block 714, method 700 may cause the data to be transmitted to the marine computing device. For instance, method 700 may transmit sensor data generated by one or more environmental sensors. In some instances, method 700 may transmit sensor data recorded in memory. In some other instances, method 700 may transmit sensor data to a computing device for storing in a database and/or for display on a display component or device.

Figure 8:
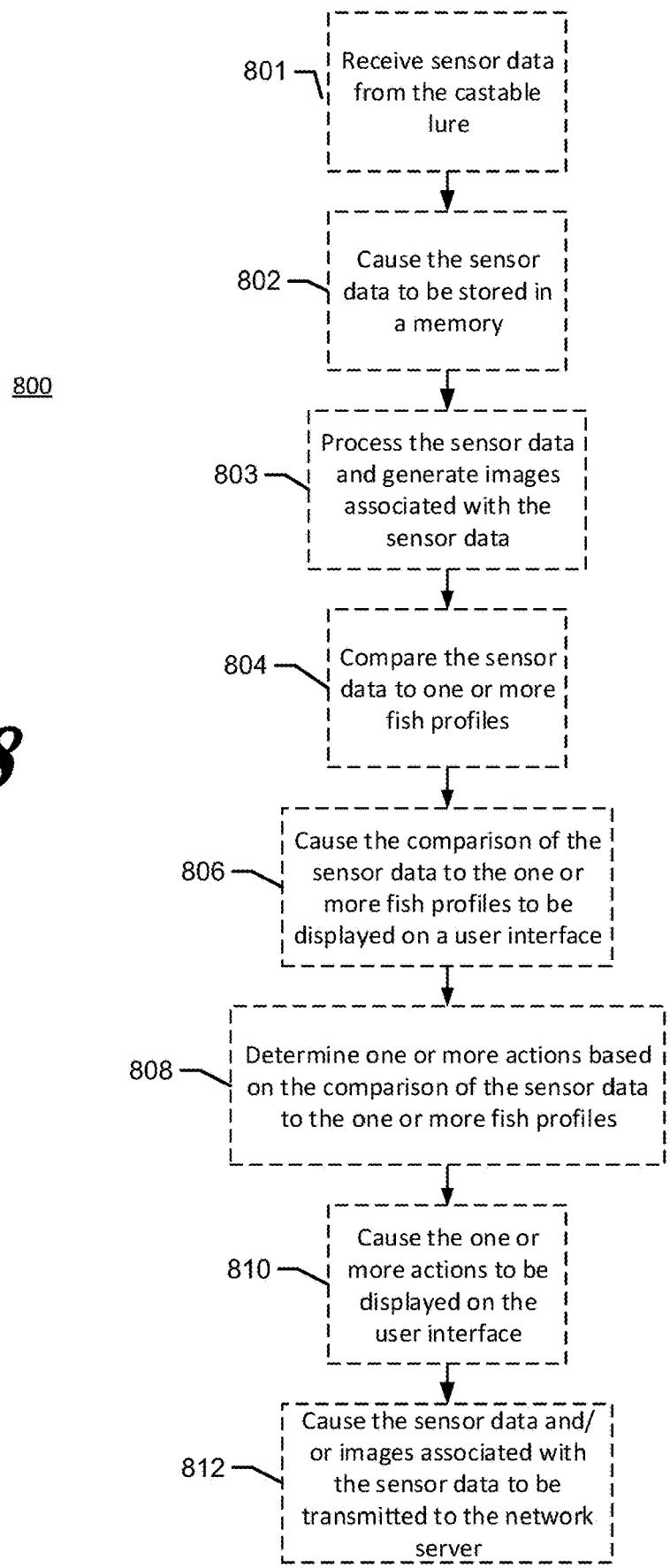

FIG. 8 illustrates a process flow diagram for a method 800 of using and/or operating a castable sensor device in accordance with implementations of techniques described herein. In one implementation, method 800 may be performed by a computing device in communication with a castable sensor device. It should be understood that while method 800 indicates a particular order of execution of operations, in some instances, certain portions of the operations may be executed in a different order, and on different systems. Further, in some other instances, additional operations or steps may be added to method 800. Similarly, some operations or steps may be omitted, as indicated by dashed lines.

At block 801, method 800 may receive sensor data from the castable sensor device. For instance, the sensor data may be received from a castable sensor device via wired or wireless network. As described herein, the received sensor data may refer to various types of environmental data including, e.g., environmental sensor data related to depth, pressure, chlorophyll concentration, oxygen concentration, temperature, light intensity, electrolyte concentration (e.g., salt content), acidity, time of flight, angular velocity, acceleration, etc. Further, in some instances, method 800 may receive sensor data generated by one or more environmental sensors at various depths in a column of water or during a cast.

At block 802, the method may cause the sensor data received at block 801 to be stored in a memory. For instance, the sonar data may be stored by a computing device, e.g., the marine electronics device, configured to store, record, and/or log sensor related data received from a castable sensor device as generated by one or more environmental sensors at various depths in a column of water.

At block 803, method 800 may process sensor data and generate images associated with sensor data, and further at block 806, method 800 may display images associated with sensor data. For instance, the computing device may include a processor and memory having instructions that cause the processor to process sensor data including generating images associated with the sensor data. The images may include chart data, such as, e.g., chart data related to various environmental conditions of a column of water at various depths. The charted environmental data may include various types of environmental data including, e.g., environmental sensor data related to depth, pressure, chlorophyll concentration, oxygen concentration, temperature, light intensity, electrolyte concentration (e.g., salt content), acidity, etc. Further, the memory may include instructions that cause the processor to display images associated with the sensor data on a display component or device.

In an example embodiment, method 800 may compare the sensor data to one or more fish profiles. For instance, the computing device may compare the sensor data to optimal fishing parameters or bands for one or more fish. Generating the images may include the comparison of the sensor data to the one or more fish profiles and causing the images to be displayed at block 806 may include causing the comparison of the sensor data to the one or more fish profiles to be displayed on a user interface.

At block 808, method 800 may determine one or more actions based on the comparison of the sensor data to the one or more fish profiles. For example increasing or decreasing crank speed, changing bait type or expected depth, changing target fish type, or the like. At block 810, method 800 may cause the one or more actions to be displayed on the user interface.

At block 812, method 800 may cause the sensor data and/or images associated with sensor data to be transmitted to a network server. For instance, method 800 may be performed by a computing device configured to upload sensor data and/or images associated with sensor data to a network server.

Figure 9:
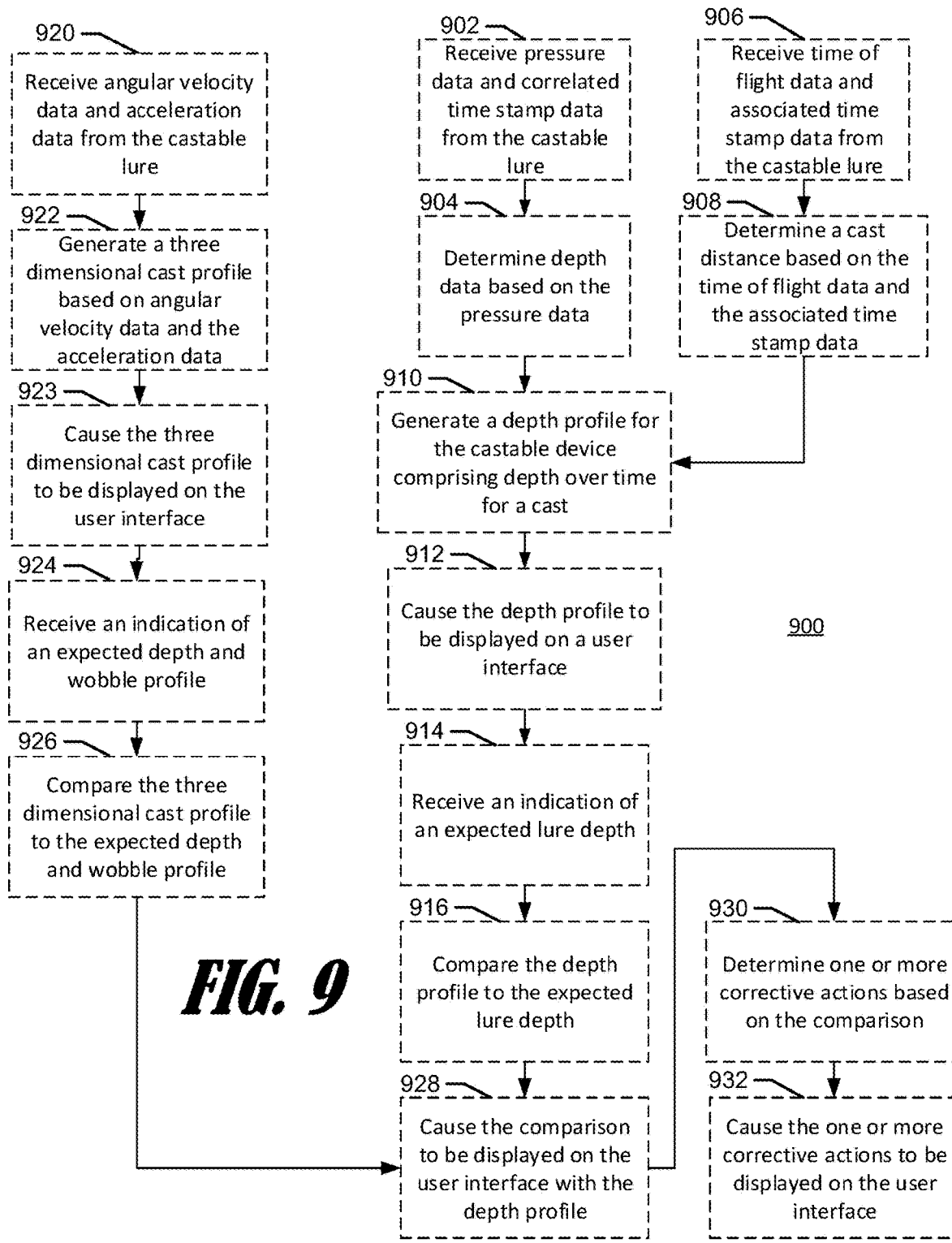

FIG. 9 illustrates an example process flow diagram for a method 900 of using and/or operating a castable sensor device in accordance with implementations of techniques described herein. In one implementation, method 900 may be performed by a computing device in communication with a castable sensor device. It should be understood that while method 900 indicates a particular order of execution of operations, in some instances, certain portions of the operations may be executed in a different order, and on different systems. Further, in some other instances, additional operations or steps may be added to method 900. Similarly, some operations or steps may be omitted, as indicated by dashed lines.

At block 902, method 900 may receive pressure data and correlated time stamp data from a castable lure. For instance, the computing device may receive the pressure data via wired or wireless transmission from the castable sensor device. At block 904, method 900 may determine depth data based on the pressure data. For instance, the castable device may compare the pressure data to a look up table or apply a conversion ratio to determine a depth associated with the pressure data.

At block 906, method 900 may receive time of flight data and associated time stamp data from the castable lure. For instance the computing device may receive the time of flight and correlated time stamp data from the castable sensor device via wired or wireless communication.

At block 908, method 900 may determine a cast distance based on the time of flight data and associated time stamp data. For instance the computing device may apply a standard distance per unit time to the time of flight or other suitable calculation of cast distance.

At block 910, method 900 may generate a depth profile for the castable device including depth over time for the cast. At block 912, method 900 may cause the depth profile to be displayed on a user interface.

At block 914, method 900 may receive an indication of an expected lure depth. For instance the computing device may receive a user input of the expected lure depth via a user interface. In an example embodiment, the user input may include a lure type and the computing device may determine the expected lure depth by comparing the lure type to a lookup table. At block 916, method 900 may compare the depth profile to the expected depth.

At block 920, method 900 may receive angular velocity data and acceleration data from the castable lure. For instance, the computing device may receive angular velocity data and acceleration data from the castable sensor device via wired or wireless communication.

At block 922, method 900 may generate a three dimensional cast profile based on the angular velocity data and the acceleration data. At block 923, method 900 may cause the three dimensional cast profile to be displayed on the user interface.

At block 924, method 900 may receive an indication of an expected lure depth and wobble profile. For instance the computing device may receive a user input of the expected lure depth and wobble profile via a user interface. In an example embodiment, the user input may include a lure type and the computing device may determine the expected lure depth and wobble profile by comparing the lure type to a lookup table. At block 926, method 900 may compare the three dimensional cast profile to the expected depth and wobble profile.

Block 928 may continue from block 916, 926, or both. At block 928, method 900 may cause the comparison(s) to be displayed on the user interface. For instance, the expected depth and/or wobble profile may be displayed with, such as overlaid on, the depth profile and/or three dimensional cast profile.

At block 930, method 900 may determine one or more corrective actions based on the comparison. For instance the computing device may determine a higher crank speed, a lower crank speed, change of bait type of depth, or the like. At block 932, method 900 may cause the corrective action to be displayed on the user interface.

Figure 10:
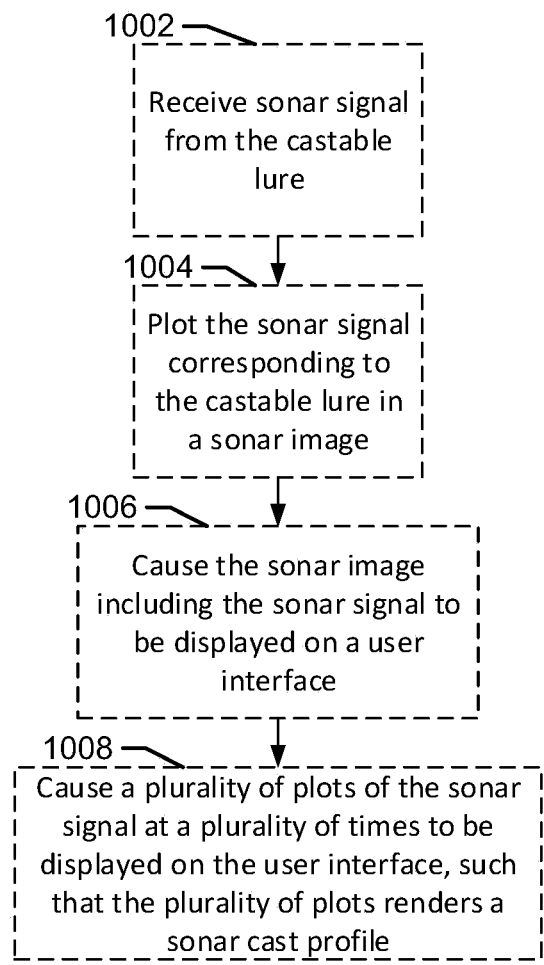

FIG. 10 illustrates an example process flow diagram for a method 1000 of using and/or operating a castable sensor device in accordance with implementations of techniques described herein. In one implementation, method 1000 may be performed by a computing device in communication with a castable sensor device. It should be understood that while method 1000 indicates a particular order of execution of operations, in some instances, certain portions of the operations may be executed in a different order, and on different systems. Further, in some other instances, additional operations or steps may be added to method 1000. Similarly, some operations or steps may be omitted, as indicated by dashed lines.

At block 1002, method 1000 may receive sonar data from the castable lure. For instance the computing device may receive a sonar signal from the castable device when submerged in the body of water via a sonar transducer.

At block 1004, method 1000 may plot the sonar signal corresponding to the castable lure in a sonar image. For instance, the computing device may receive a sonar return including the sonar signal, process the sonar return to generate a sonar image including plotting the location of the sonar signal of the castable sensor device.

At block 1006, method 1000 may cause the sonar image including the sonar signal to be displayed on a user interface. At block 1008, method 1000 may cause a plurality of plots of the sonar signal at a plurality of times to be displayed on the user interface, such that the plurality of plots renders a sonar cast profile. For instance, the computing device may process a plurality of sonar returns over a period of time, which include the sonar signal of the castable sensor device. The computing device may plot a plurality of the sonar signals in a sonar image to generate a sonar cast profile of the castable sensor device traveling through the body of water.

Figure 11:
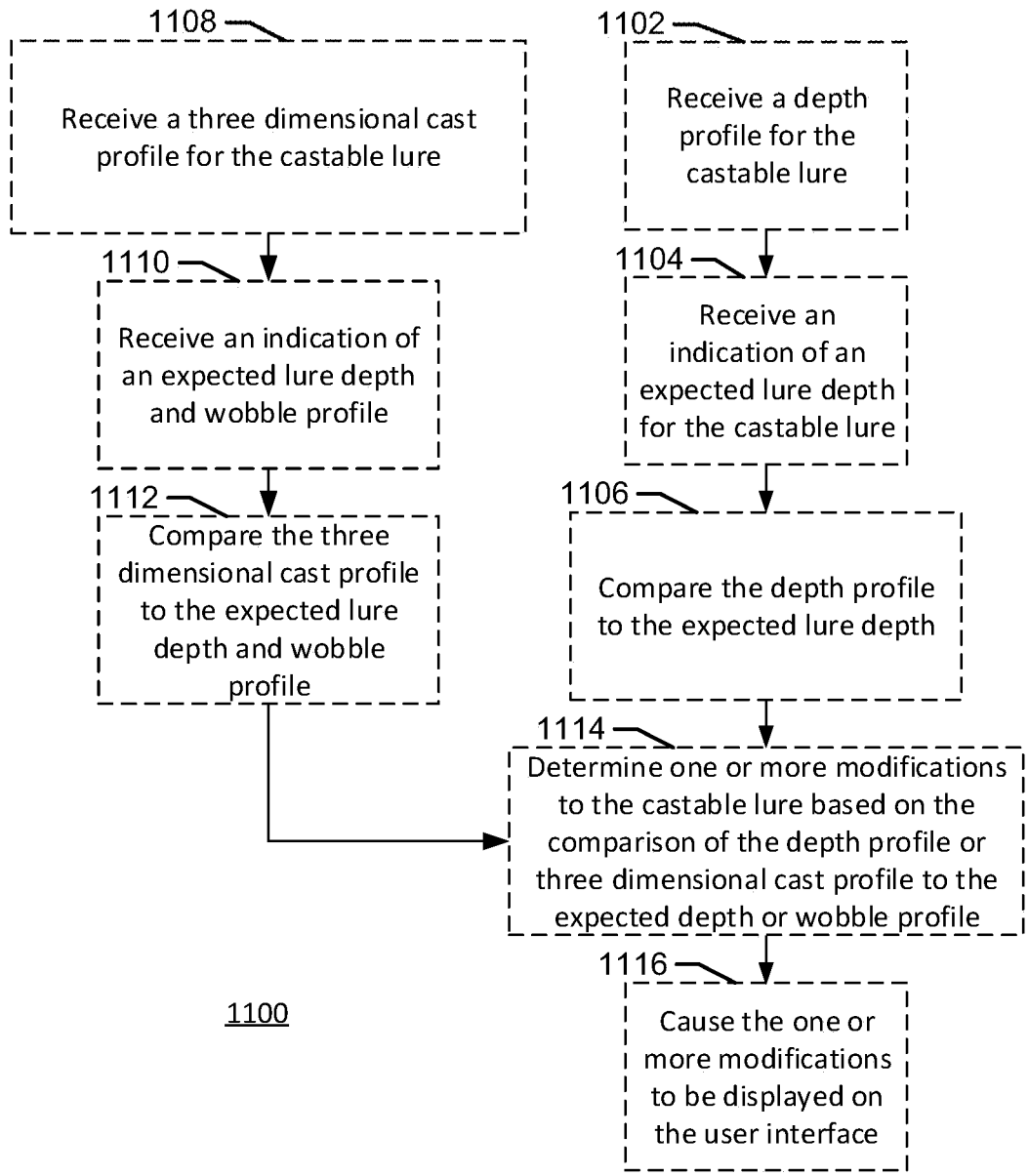

FIG. 11 illustrates an example process flow diagram for a method 1100 of using and/or operating a castable sensor device in accordance with implementations of techniques described herein. In one implementation, method 1100 may be performed by a computing device in communication with a castable sensor device. It should be understood that while method 1000 indicates a particular order of execution of operations, in some instances, certain portions of the operations may be executed in a different order, and on different systems. Further, in some other instances, additional operations or steps may be added to method 1100. Similarly, some operations or steps may be omitted, as indicated by dashed lines.

At block 1102, method 1100 may receive a depth profile for a castable lure, e.g. castable device. For instance, the network server may receive one or more depth profiles or an average depth profile from the computing device via wired or wireless communication. In some embodiments, the network server may receive the depth or pressure data correlated to the time stamp data and generate the depth profile.

At block 1104, method 1100 may receive an indication of an expected depth for the castable lure. For instance the network server may receive a lure model number or expected depth entered by a user of the computing device. At block 1106, method 1100 may compare the depth profile to the expected lure depth.

At block 1108, method 1100 may receive a three dimensional cast profile for the castable lure. For instance, the network server may receive one or more three dimensional cast profiles or a three dimensional cast profile from the computing device via wired or wireless communication. In some embodiments, the network server may receive the angular velocity and acceleration data correlated to the time stamp data and generate the three dimensional cast profile.

At block 1110, method 1100 may receive an indication of an expected depth and wobble profile for the castable lure. For instance the network server may receive a lure model number or expected depth and/or wobble profile entered by a user of the computing device. At block 1112, method 1100 may compare the three dimensional cast profile to the expected lure depth and wobble profile.

At block 1114, method 1100 may determine one or more modifications to the castable lure based on the comparison of the depth profile or three dimensional cast profile to the expected depth and/or wobble profile. For instance, the network server may determine that the bill of the castable device needs to be elongated or shortened to achieve the expected depth, the bill width should be widened or narrowed to achieve the expected wobble, a change to the contour of the body of the castable lure should be changed to achieve the expected wobble, or a distribution or total weight of the castable lure should be changed to achieve the expected wobble.

At block 1116, method 1100 may cause the one or more modifications to be displayed on a user interface. For instance, the network server may provide a text based indication of the modifications. In some embodiments, the network server may cause a model of the lure to be modified based on the one or modifications and display the modified model and/or the changes to the model. In an example embodiment, the modified model may be sent to a manufacturing device to generate one or more castable lures based on the modified model.

Example Computing System

Implementations of various technologies described herein may be operational with numerous general purpose or special purpose computing system environments or configurations. Examples of well-known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, tablets, wearable computers, cloud computing systems, virtual computers, marine electronics devices, and the like.

The various technologies described herein may be implemented in the general context of computer-executable instructions, such as program modules, being executed by a computer. Generally, program modules include routines, programs, objects, components, data structures, etc. that perform particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may be implemented in the context of marine electronics, such as devices found in marine vessels and/or navigation systems. Ship instruments and equipment may be connected to the computing systems described herein for executing one or more navigation technologies. The computing systems may be configured to operate using various radio frequency technologies and implementations, such as sonar, radar, GPS, and like technologies.

The various technologies described herein may also be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

Example Marine Electronics Device

Figure 12:
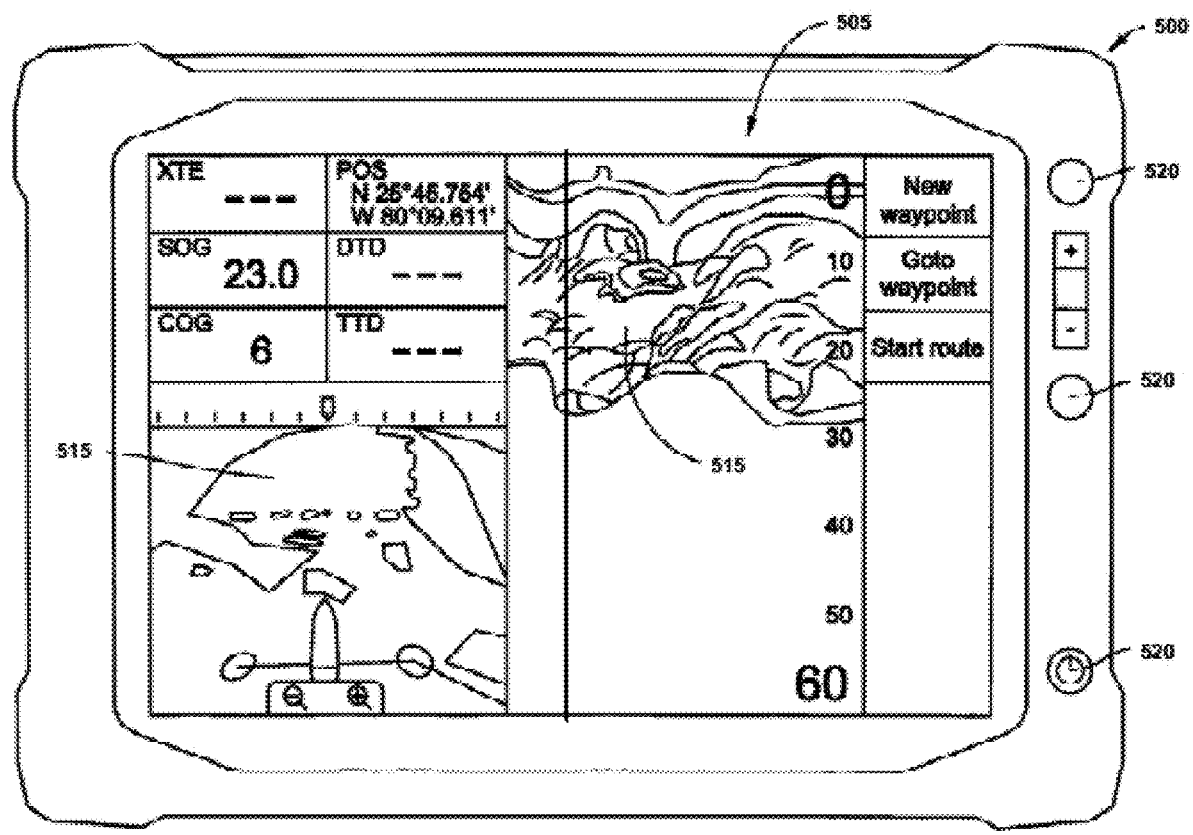
FIG. 12 illustrates a schematic of an example marine electronics device in accordance with various implementations described herein.

FIG. 12 illustrates an instance schematic of a marine electronics device 500, such as computing device 122, in accordance with implementations of various techniques described herein. The marine electronics device 500 includes a screen 505. In some instances, the screen 505 may be sensitive to touching by a finger. In other instances, the screen 505 may be sensitive to the body heat from the finger, a stylus, or responsive to a mouse. In various implementations, the marine electronics device 500 may be attached to various buses and/or networks, such as, e.g., a National Marine Electronics Association (NMEA) bus or network. The marine electronics device 500 may send or receive data to or from another device attached to the NMEA 2000 bus. For instance, the marine electronics device 500 may transmit commands and receive data from a motor or a sensor using an NMEA 2000 bus. In some implementations, the marine electronics device 500 may be capable of steering a vessel and controlling the speed of the vessel, i.e., autopilot. For instance, one or more waypoints may be input to the marine electronics device 500, and the marine electronics device 500 may be configured to steer the vessel to the one or more waypoints. Further, the marine electronics device 500 may be configured to transmit and/or receive NMEA 2000 compliant messages, messages in a proprietary format that do not interfere with NMEA 2000 compliant messages or devices, and/or messages in any other format. In various other implementations, the marine electronics device 400 may be attached to various other communication buses and/or networks configured to use various other types of protocols that may be accessed via, e.g., NMEA 2000, NMEA 0183, Ethernet, Proprietary wired protocol, etc.

The marine electronics device 500 may be operational with numerous general purpose or special purpose computing system environments and/or configurations. The marine electronics device 500 may include any type of electrical and/or electronics device capable of processing data (including, e.g., various environmental sensor type data) and information via a computing system. The marine electronics device 500 may include various marine instruments, such that the marine electronics device 500 may use the computing system to display and/or process the one or more types of marine electronics data. The device 500 may display marine electronic data 515, such as, e.g., sensor data and images associated with sensor data. The marine electronic data types 515 may include various chart data, radar data, sonar data, steering data, dashboard data, navigation data, fishing data, engine data, and the like. The marine electronics device 500 may include one or more buttons 520, which may include physical buttons or virtual buttons, or some combination thereof. The marine electronics device 500 may receive input through a screen 505 sensitive to touch or buttons 520.

In some implementations, according to various techniques described herein, the marine electronics device 500 may be configured to simultaneously display images associated with one or more environmental sensors, an array of environmental sensors, and the like. For instance, the marine electronics device 500 may be configured to simultaneously display images associated with a plurality of environmental sensors, including environmental sensor data related to various environmental conditions of a column of water, such as, e.g., depth, pressure, chlorophyll concentration, oxygen concentration, temperature, light intensity, electrolyte concentration (e.g., salt content), acidity, etc. In some instances, in various display modes of operation, the marine electronics device 500 may be configured to simultaneously display images associated with environmental sensor data on the screen 505. Further, environmental data related to detected environmental conditions of water may be displayed on the screen 505 of the marine electronics device 500 by overlaying various environmental data on chart and sonar images. In some instances, various environmental data may include current levels of environmental conditions at particular depths, upper and lower boundary levels at particular depths, average levels through a water column, and any changes that occur throughout sensor use during a particular time period or interval.

The marine electronics device 500 may be configured as a computing system having a central processing unit (CPU), a system memory, a graphics processing unit (GPU), and a system bus that couples various system components including the system memory to the CPU. In various implementations, the computing system may include one or more CPUs, which may include a microprocessor, a microcontroller, a processor, a programmable integrated circuit, or a combination thereof. The CPU may include an off-the-shelf processor such as a Reduced Instruction Set Computer (RISC), or a Microprocessor without Interlocked Pipeline Stages (MIPS) processor, or a combination thereof. The CPU may also include a proprietary processor.

The GPU may be a microprocessor specifically designed to manipulate and implement computer graphics. The CPU may offload work to the GPU. The GPU may have its own graphics memory, and/or may have access to a portion of the system memory. As with the CPU, the GPU may include one or more processing units, and each processing unit may include one or more cores.

The CPU may provide output data to a GPU. Further, the GPU may generate user interfaces (UIs) including graphical user interfaces (GUIs) that provide, present, and/or display the output data. The GPU may also provide objects, such as menus, in the GUI. In some instances, a user may provide input by interacting with objects, and the GPU may receive input from interaction with objects and provide the received input to the CPU. Further, in some instances, a video adapter may be provided to convert graphical data into signals for a monitor, such as, e.g., a multi-function display (MFD 500). The monitor (i.e., MFD 500) includes a screen 505. In various instances, the screen 505 may be sensitive to touch by a human finger, and/or the screen 505 may be sensitive to body heat from a human finger, a stylus, and/or responsive to a mouse.

The system bus may be any of several types of bus structures, including a memory bus or memory controller, a peripheral bus, and a local bus using any of a variety of bus architectures. By way of instance, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory may include a read only memory (ROM) and a random access memory (RAM). A basic input/output system (BIOS), containing the basic routines that help transfer information between elements within the computing system, such as during start-up, may be stored in the ROM.

The computing system may further include a hard disk drive interface for reading from and writing to a hard disk, a memory card reader for reading from and writing to a removable memory card, and an optical disk drive for reading from and writing to a removable optical disk, such as a CD ROM or other optical media. The hard disk, the memory card reader, and the optical disk drive may be connected to the system bus by a hard disk drive interface, a memory card reader interface, and an optical drive interface, respectively. The drives and their associated computer-readable media may provide nonvolatile storage of computer-readable instructions, data structures, program modules and other data for the computing system.

Although the computing system is described herein as having a hard disk, a removable memory card and a removable optical disk, it should be appreciated by those skilled in the art that the computing system may also include other types of computer-readable media that may be accessed by a computer. For instance, such computer-readable media may include computer storage media and communication media. Computer storage media may include volatile and non-volatile, and removable and non-removable media implemented in any method or technology for storage of information, such as computer-readable instructions, data structures, program modules, software modules, or other data. Computer-readable storage media may include non-transitory computer-readable storage media. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system. Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of instance, and not limitation, communication media may include wired media such as a wired network or direct-wired connection, and wireless media such as acoustic, radio frequency (RF), infrared (IR), and other wireless media. The computing system may include a host adapter that connects to a storage device via a small computer system interface (SCSI) bus, Fiber Channel bus, eSATA bus, or using any other applicable computer bus interface.

The computing system can also be connected to a router to establish a wide area network (WAN) with one or more remote computers. The router may be connected to the system bus via a network interface. The remote computers can also include hard disks that store application programs. In another implementation, the computing system may also connect to the remote computers via local area network (LAN) or the WAN. When using a LAN networking environment, the computing system may be connected to the LAN through the network interface or adapter. The LAN may be implemented via a wired connection or a wireless connection. The LAN may be implemented using Wi-Fi™ technology, cellular technology, Bluetooth™ technology, satellite technology, or any other implementation known to those skilled in the art. The network interface may also utilize remote access technologies (e.g., Remote Access Service (RAS), Virtual Private Networking (VPN), Secure Socket Layer (SSL), Layer 2 Tunneling (L2T), or any other suitable protocol). In some instances, these remote access technologies may be implemented in connection with the remote computers. It will be appreciated that the network connections shown are exemplary and other means of establishing a communications link between the computer systems may be used.

A number of program modules may be stored on the hard disk, memory card, optical disk, ROM or RAM, including an operating system, one or more application programs, and program data. In certain implementations, the hard disk may store a database system. The database system could include, for instance, recorded points. The application programs may include various mobile applications ("apps") and other applications configured to perform various methods and techniques described herein. The operating system may be any suitable operating system that may control the operation of a networked personal or server computer.

A user may enter commands and information into the computing system through input devices such as buttons, which may be physical buttons, virtual buttons, or combinations thereof. Other input devices may include a microphone, a mouse, or the like (not shown). These and other input devices may be connected to the CPU through a serial port interface coupled to system bus, but may be connected by other interfaces, such as a parallel port, game port or a universal serial bus (USB).

Certain implementations may be configured for connection to a GPS receiver system and/or a marine electronics device or system. The GPS system and/or marine electronics device or system may be connected via a network interface. For instance, the GPS receiver system may be used to determine position data for the vessel on which the marine electronics device 500 is disposed. Further, the GPS receiver system may transmit position data to the marine electronics device 500. In other instances, any positioning system known to those skilled in the art may be used to determine and/or provide the position data for the marine electronics device 500.

In various implementations, the marine electronics device or system may include one or more components disposed at various locations on a vessel. Such components may include one or more data modules, sensors, instrumentation, and/or any other devices known to those skilled in the art that may transmit various types of data to the marine electronics device 500 for processing and/or display. The various types of data transmitted to the marine electronics device 500 may include marine electronics data and/or other data types known to those skilled in the art. The marine electronics data received from the marine electronics device or system may include chart data, sonar data, structure data, radar data, navigation data, position data, heading data, automatic identification system (AIS) data, Doppler data, speed data, course data, or any other type known to those skilled in the art.

In one implementation, the marine electronics device or system may include a radar sensor for recording the radar data and/or the Doppler data, a compass heading sensor for recording the heading data, and a position sensor for recording the position data. In a further implementation, the marine electronics device or system may include a sonar transducer for recording the sonar data, an AIS transponder for recording the AIS data, a paddlewheel sensor for recording the speed data, and/or the like.

The marine electronics device 500 may receive external data via a LAN or a WAN. In some implementations, external data may relate to information not available from various marine electronics systems. The external data may be retrieved from the Internet or any other source. The external data may include atmospheric temperature, atmospheric pressure, tidal data, weather, temperature, moon phase, sunrise, sunset, water levels, historic fishing data, and/or various other fishing data.

In one implementation, the marine electronics device 500 may be a multi-function display (MFD) unit, such that the marine electronics device 500 may be capable of displaying and/or processing multiple types of marine electronics data. FIG. 12 illustrates a schematic diagram of an MFD unit in accordance with implementations of various techniques described herein. In particular, the MFD unit may include the computing system, the monitor (MFD 500), the screen 505, and the buttons such that they may be integrated into a single console.

The discussion of the present disclosure is directed to certain specific implementations. It should be understood that the discussion of the present disclosure is provided for the purpose of enabling a person with ordinary skill in the art to make and use any subject matter defined herein by the subject matter of the claims.

It should be intended that the subject matter of the claims not be limited to the implementations and illustrations provided herein, but include modified forms of those implementations including portions of the implementations and combinations of elements of different implementations within the scope of the claims. It should be appreciated that in the development of any such implementation, as in any engineering or design project, numerous implementation-specific decisions should be made to achieve a developers' specific goals, such as compliance with system-related and business related constraints, which may vary from one implementation to another. Moreover, it should be appreciated that such a development effort maybe complex and time consuming, but would nevertheless be a routine undertaking of design, fabrication, and manufacture for those of ordinary skill having benefit of this disclosure. Nothing in this application should be considered critical or essential to the claimed subject matter unless explicitly indicated as being "critical" or "essential."

Reference has been made in detail to various implementations, instances of which are illustrated in the accompanying drawings and figures. In the following detailed description, numerous specific details are set forth to provide a thorough understanding of the present disclosure. However, the present disclosure may be practiced without these specific details. In other instances, well-known methods, procedures, components, circuits and networks have not been described in detail so as not to unnecessarily obscure aspects of the embodiments.

It should also be understood that, although the terms first, second, etc. may be used herein to describe various elements, these elements should not be limited by these terms. These terms are only used to distinguish one element from another. For instance, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations and is not intended to limit the present disclosure. As used in the description of the present disclosure and appended claims, the singular forms "a," "an," and "the" are intended to include the plural forms as well, unless the context clearly indicates otherwise. The term "and/or" as used herein refers to and encompasses any and all possible combinations of one or more of the associated listed items. The terms "includes," "including," "comprises," and/or "comprising," when used in this specification, specify a presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

While the foregoing is directed to implementations of various techniques described herein, other and further implementations may be devised without departing from the basic scope thereof, which may be determined by the claims that follow.

Although the subject matter has been described in language specific to structural features and/or methodological acts, it is to be understood that the subject matter defined in the appended claims is not necessarily limited to the specific features or acts described above. Rather, the specific features and acts described above are disclosed as instance forms of implementing the claims.

What is claimed is:

1. A sensor assembly for a castable lure comprising:
   a pressure sensor configured to measure a water pressure applied to the castable lure when deployed in an underwater environment;
   a transceiver configured to transmit data from the castable lure to a marine electronic device;
   a processor;
   a time of flight sensor configured to measure a time of flight of the castable lure from an initiation of a cast to when the castable lure strikes water; and
   a memory including computer program code configured to, when executed on the processor, cause the processor to:
      receive pressure data from the pressure sensor;
      receive time of flight data from the time of flight sensor;
      correlate the pressure data with time stamp data to generate correlated time stamp data;
      associate the time of flight data with the pressure data and the correlated time stamp data;
      cause the pressure data and correlated time stamp data to be stored in the memory;
      determine a data connection status between the transceiver and the marine electronic device; and
      in response to determining that a data connection exists between the transceiver and the marine electronic device, cause the time of flight data, the pressure data and the correlated time stamp data to be transmitted to the marine electronic device, wherein the pressure data and the correlated time stamp data correspond to a depth profile for the cast of the castable lure, wherein the depth profile corresponds to a travel path of the castable lure during the cast, wherein the time of flight data corresponds to a cast distance of the depth profile.

2. The sensor assembly of claim 1 further comprising:
   a gyroscope configured to measure angular velocity of the castable lure; and
   an accelerometer configured to measure acceleration of the castable lure;
   wherein the memory and the computer program code are further configured to cause the processor to:
      receive angular velocity data from the gyroscope and acceleration data from the accelerometer;
      associate the angular velocity data and the acceleration data with the time stamp data; and
      cause the angular velocity data and the acceleration data to be transmitted with the pressure data and correlated time stamp data, wherein the pressure data, the angular velocity data, the acceleration data, and the correlated time stamp data correspond to a three-dimensional cast profile for the cast of the castable lure.

3. The sensor assembly of claim 1, further comprising:
   a sonar transducer configured to emit a sonar signal into the underwater environment when the castable lure is at least partially submerged.

4. The sensor assembly of claim 3, wherein the transceiver utilizes the sonar transducer to transmit the pressure data and the correlated time stamp data to the marine electronic device.

5. The sensor assembly of claim 1, wherein the transceiver comprises a Bluetooth transceiver.

6. The sensor assembly of claim 1 further comprising:
   at least one of a chlorophyll sensor, an oxygen sensor, a temperature sensor, a light sensor, an electrolyte sensor, and an acidity sensor.

7. A marine electronic device comprising:
   a communication interface configured to receive data from a castable lure, wherein the castable lure comprises a pressure sensor configured to measure a water pressure applied to the castable lure when deployed in an underwater environment;
   a processor; and
   a memory including computer program code configured to, when executed on the processor, cause the processor to:
      receive pressure data and correlated time stamp data from the castable lure;
      determine depth data based on the pressure data;
      determine a depth profile for the castable lure comprising depth over time for a cast, wherein the depth profile is determined using depth data and the correlated time stamp data;
      generate a depth profile image that illustrates a current depth of the castable lure and one or more past depths of the castable lure; and cause the depth profile image to be displayed on a user interface, wherein the depth profile corresponds to a travel path of the castable lure during the cast.

8. The marine electronic device of claim 7, wherein the memory and the computer program code are further configured to cause the processor to:
receive an indication of an expected lure depth;
compare the depth profile to the expected lure depth; and
cause the comparison of the depth profile to the expected lure depth to be displayed on the user interface with the depth profile.

9. The marine electronic device of claim 8, wherein the memory and the computer program code are further configured to cause the processor to:
determine one or more corrective actions based on the comparison of the depth profile to the expected lure depth; and
cause the one or more corrective actions to be displayed on the user interface.

10. The marine electronic device of claim 7, wherein the castable lure further comprises a time of flight sensor configured to measure a time of flight of the castable lure from an initiation of the cast to the castable lure striking water, and
wherein the memory and the computer program code are further configured to cause the processor to:
receive time of flight data;
associate the time of flight data with the correlated time stamp data; and
determine a cast distance based on the time of flight data and the correlated time stamp data;
wherein the depth profile further comprises the cast distance.

11. The marine electronic device of claim 7, wherein the castable lure further comprises a gyroscope configured to measure angular velocity of the castable lure and an accelerometer configured to measure acceleration of the castable lure; and
wherein the memory and the computer program code are further configured to cause the processor to:
receive angular velocity data and acceleration data with the correlated time stamp data from the castable lure; and
generate a three-dimensional cast profile based on the angular velocity data and the acceleration data with the correlated time stamp data.

12. The marine electronic device of claim 11, wherein the memory and the computer program code are further configured to cause the processor to:
receive an indication of an expected lure depth and wobble profile;
compare the three-dimensional cast profile to the expected lure depth and wobble profile; and
cause the comparison of the three-dimensional cast profile to the expected lure depth and wobble profile to be displayed on the user interface.

13. The marine electronic device of claim 7, wherein the castable lure comprises a sonar transducer configured to emit a sonar signal into the underwater environment when the castable lure is at least partially submerged; and
wherein the memory and the computer program code are further configured to cause the processor to:
receive the sonar signal from the castable lure;
plot the sonar signal corresponding to the castable lure in a sonar image; and
cause the sonar image including the sonar signal to be displayed on a user interface.

14. The marine electronic device of claim 13, wherein the memory and the computer program code are further configured to cause the processor to:
cause a plurality of plots of the sonar signal at a plurality of times to be displayed on the user interface, such that the plurality of plots renders a sonar cast profile in the sonar image.

15. The marine electronic device of claim 7, wherein the data is received from the castable lure via sonar signal.

16. The marine electronic device of claim 7, wherein displaying the depth profile on the user interface comprises overlaying the depth profile on a sonar image or three-dimensional chart.

17. A system comprising:
a castable lure comprising:
a pressure sensor configured to measure a water pressure applied to the castable lure when deployed in an underwater environment;
a transceiver configured to transmit marine data from the castable lure to a marine electronic device;
a lure processor; and
a lure memory including computer program code configured to, when executed on the lure processor, cause the lure processor to:
receive pressure data from the pressure sensor;
correlate the pressure data with time stamp data to generate correlated time stamp data;
cause the pressure data and correlated time stamp data to be stored in the lure memory;
determine a data connection status between the transceiver and the marine electronic device; and
in response to determining that a data connection exists between the transceiver and the marine electronic device, causing the pressure data and the correlated time stamp data to be transmitted to the marine electronic device; and
a marine electronic device comprising:
a communication interface configured to receive data from the castable lure;
a device processor; and
a device memory including computer program code configured to, when executed on the device processor, cause the device processor to:
receive pressure data and correlated time stamp data from the castable lure;
determine depth data based on the pressure data;
determine a depth profile for the castable lure comprising depth over time for a cast, wherein the depth profile is determined using depth data and the correlated time stamp data; and
generate a depth profile image that illustrates a current depth of the castable lure and one or more past depths of the castable lure.

18. The system of claim 17 further comprising:
a remote server comprising
a server processor; and
a server memory including computer program code configured to, when executed on the server processor, cause the server processor to:
receive the depth profile for the castable lure;
receive an indication of an expected lure depth for the castable lure;
compare the depth profile to the expected lure depth; and
determine one or more recommended modifications to the castable lure based on the comparison of the depth profile to the expected lure profile.

19. The system of claim 17, wherein the castable lure further comprises a gyroscope configured to measure angular velocity of the castable lure and an accelerometer configured to measure acceleration of the castable lure;
- wherein the device memory and the computer program code are further configured to cause the device processor to:
  - receive angular velocity data and acceleration data with the correlated time stamp data from the castable lure; and
  - generate a three-dimensional cast profile based on the angular velocity data and the acceleration data with the correlated time stamp data; and
- wherein the server memory and the computer program code are further configured to cause the server processor to:
  - receive an indication of an expected lure depth and wobble profile;
  - compare the three-dimensional cast profile to the expected lure depth and wobble profile; and
  - determine one or more recommended modifications to the castable lure based on the comparison of the three-dimensional cast profile to the expected lure depth and wobble profile.

20. A sensor assembly for a castable lure comprising:
- a pressure sensor configured to measure a water pressure applied to the castable lure when deployed in an underwater environment;
- a transceiver configured to transmit data from the castable lure to a marine electronic device;
- a processor;
- a sonar transducer configured to emit a sonar signal into the underwater environment when the castable lure is at least partially submerged; and
- a memory including computer program code configured to, when executed on the processor, cause the processor to:
  - receive pressure data from the pressure sensor;
  - correlate the pressure data with time stamp data to generate correlated time stamp data;
  - cause the pressure data and correlated time stamp data to be stored in the memory;
  - determine a data connection status between the transceiver and the marine electronic device; and
  - in response to determining that a data connection exists between the transceiver and the marine electronic device, cause the pressure data and the correlated time stamp data to be transmitted to the marine electronic device, wherein the pressure data and correlated time stamp data correspond to a depth profile for a cast of the castable lure, wherein the depth profile corresponds to a travel path of the castable lure during the cast;
- wherein the transceiver utilizes the sonar transducer to transmit the pressure data and the correlated time stamp data to the marine electronic device.

21. A sensor assembly for a castable lure comprising:
- a pressure sensor configured to measure a water pressure applied to the castable lure when deployed in an underwater environment;
- a transceiver configured to transmit data from the castable lure to a marine electronic device;
- a processor;
- at least one of a chlorophyll sensor, an oxygen sensor, a temperature sensor, a light sensor, an electrolyte sensor, and an acidity sensor; and
- a memory including computer program code configured to, when executed on the processor, cause the processor to:
  - receive pressure data from the pressure sensor;
  - correlate the pressure data with time stamp data to generate correlated time stamp data;
  - cause the pressure data and correlated time stamp data to be stored in the memory;
  - determine a data connection status between the transceiver and the marine electronic device; and
  - in response to determining that a data connection exists between the transceiver and the marine electronic device, cause the pressure data and the correlated time stamp data to be transmitted to the marine electronic device, wherein the pressure data and correlated time stamp data correspond to a depth profile for a cast of the castable lure, wherein the depth profile corresponds to a travel path of the castable lure during the cast.

* * * * *